(12) United States Patent
Yoakim et al.

(10) Patent No.: US 7,105,510 B2
(45) Date of Patent: Sep. 12, 2006

(54) NON-NUCLEOSIDE REVERSE TRANSCRIPTASE INHIBITORS

(75) Inventors: Christiane Yoakim, Laval (CA); Eric Malenfant, Rosemère (CA); Bounkham Thavonekham, Longueuil (CA); William Ogilvie, Ottawa (CA); Robert Déziel, Ville Mont-Royal (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 295 days.

(21) Appl. No.: 10/662,856

(22) Filed: Sep. 15, 2003

(65) Prior Publication Data

US 2004/0106791 A1 Jun. 3, 2004

Related U.S. Application Data

(60) Provisional application No. 60/411,785, filed on Sep. 19, 2002.

(51) Int. Cl.
C07D 471/14 (2006.01)
A61K 31/55 (2006.01)
A61P 31/18 (2006.01)

(52) U.S. Cl. ..................... 514/220; 540/495
(58) Field of Classification Search ............... 540/495; 514/220
See application file for complete search history.

(56) References Cited

U.S. PATENT DOCUMENTS

| 5,705,499 A | 1/1998 | Cywin et al. |
| 2003/0069226 A1 | 4/2003 | Ogilvie et al. |
| 2003/0171363 A1 | 9/2003 | Ogilvie et al. |

OTHER PUBLICATIONS

Janice M. Klunder et al; Novel Nonnucleoside Inhibitors of HIV-1 Reverse Transcriptase. 7. 8-Arylethyldipyridodiazepinones as Potent Broad-Spectrum Inhibitors of Wild-Type and Mutant Enzymes; J. Med. Chem 1998 vol. 41 pp. 2960-2971; American Chemical Society.

Charles L. Cywin et al; Novel Nonnucleoside Inhibitors of HIV-1 Reverse Transcriptase. 8. 8-Aryloxymethyl- and 8-Arylthiomethyldipyridodiazepinones; J. Med. Chem 1998 vol. 41 pp. 2972-2984; American Chemical Society.

*Primary Examiner*—Bruck Kifle
(74) *Attorney, Agent, or Firm*—Michael P. Morris; Mary-Ellen M. Devlin; Alan R. Stempel

(57) ABSTRACT

Compounds represented by formula I:

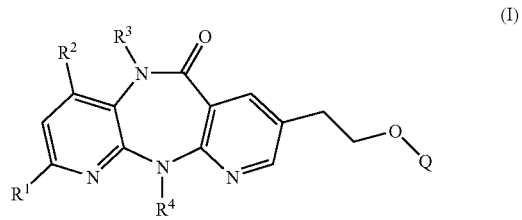

wherein $R^1$ is H, halogen, $(C_{1-4})$alkyl, $O(C_{1-4})$alkyl, and haloalkyl; $R^2$ is H or $(C_{1-4})$alkyl; $R^3$ is H or $(C_{1-4})$alkyl; $R^4$ is $(C_{1-4})$alkyl, $(C_{1-4})$alkyl$(C_{3-7})$cycloalkyl, or $(C_{3-7})$cycloalkyl; and Q is a fused phenyl-5 or 6-membered saturated heterocycle having one to two heteroatoms selected from O and N, said Q being optionally substituted with hydroxy, or $(C_{1-4})$alkyl which in turn maybe optionally substituted with pyridinyl-N-oxide or C(O)OR wherein R is H or $(C_{1-4})$alkyl; or a salt thereof. The compounds have inhibitory activity against Wild Type, and single and double mutants strains, of HIV.

10 Claims, No Drawings

NON-NUCLEOSIDE REVERSE TRANSCRIPTASE INHIBITORS

TECHNICAL FIELD OF THE INVENTION

The invention relates to novel compounds and pharmaceutically acceptable salts thereof, their use, either alone or in combination with other therapeutic agents, in the treatment or prophylaxis of HIV infection, and to pharmaceutical compositions comprising these compounds that are active against NNRTI resistant mutants.

BACKGROUND OF THE INVENTION

The disease known as acquired immune deficiency syndrome (AIDS) is caused by the human immunodeficiency virus (HIV), particularly the strain known as HIV-1. In order for HIV to be replicated by a host cell, the information of the viral genome must be integrated into the host cell's DNA. However, HIV is a retrovirus, meaning that its genetic information is in the form of RNA. The HIV replication cycle therefore requires a step of transcription of the viral genome (RNA) into DNA, which is the reverse of the normal chain of events. An enzyme that has been aptly dubbed reverse transcriptase (RT) accomplishes the transcription of the viral RNA into DNA. The HIV virion includes a copy of RT along with the viral RNA.

Reverse transcriptase has three known enzymatic functions; it acts as an RNA-dependent DNA polymerase, as a ribonuclease, and as a DNA-dependent DNA polymerase. Acting as an RNA-dependent DNA polymerase, RT transcribes a single-stranded DNA copy from the viral RNA. Acting as a ribonuclease, RT destroys the original viral RNA, and frees the DNA just produced from the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds that inhibit the enzymatic functions of HIV-1 reverse transcriptase will inhibit replication of HIV-1 in infected cells. Such compounds are useful in the prevention or treatment of HIV-1 infection in human subjects, as demonstrated by known RT inhibitors such as 3'-azido-3'-deoxythymidine (AZT), 2',3'-dideoxyinosine (ddI), 2',3'-dideoxycytidine (ddC), d4T, 3TC, Nevirapine, Delavirdine, Efavirenz, Abacavir, and Tenofovir, the main drugs thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterized, and resistance to known therapeutic agents is believed to be due to mutations in the RT gene. One of the more commonly observed mutants clinically for the non-nucleoside reverse transcriptase inhibitors, is the Y181C mutant, in which a tyrosine (Y), at codon 181, has been mutated to a cysteine (C) residue. Other mutants, which emerge with increasing frequency during treatment using known NNRTI antivirals, include single mutants K103N, V106A, G190A, Y188C, and P236L, and double mutants K103N/Y181C, K103N/P225H, K103N/V108I and K103N/L100I.

As antiviral use in therapy and prevention of HIV infection continues, the emergence of new resistant strains is expected to increase. There is therefore an ongoing need for new inhibitors of RT, which have different patterns of effectiveness against the various resistant mutants.

Compounds having tricyclic structures, which are inhibitors of HIV-1, are described in U.S. Pat. No. 5,366,972. Other inhibitors of HIV-1 reverse transcriptase are described in Hargrave et al., J. Med Chem., 34, 2231 (1991), Cywin et al., J. Med. Chem., 41, 2972 (1998) and Klunder et al., J. Med. Chem., 41, 2960 (1998).

U.S. Pat. No. 5,705,499 proposes 8-arylalkyl- and 8-arylheteroalkyl-5,11-dihydro-6H-dipyrido[3,2-b:2',3'-e][1,4]diazepines as inhibitors of RT. The exemplified compounds are shown to have some activity against HIV WT reverse transcriptase.

WO 01/96338A1, equivalent to U.S. Pat. No. 6,420,359 B1, discloses diazepine structures having quinoline and quinoline-N-oxide substituents as inhibitors of RT. The exemplified compounds have activity against HIV, WT, single and double mutant strains.

WO 02/076982 and WO 03/011862 also disclose diazepine-based structures having different substituents and different inhibitory profile against resistant mutants than the compounds of the invention.

SUMMARY OF THE INVENTION

The invention provides novel fused ring-containing compounds that are potent inhibitors of wild-type (WT) and double mutant strains of HIV-1 RT, particularly the double mutation K103N/Y181C.

In a first aspect the invention provides a compound represented by formula I:

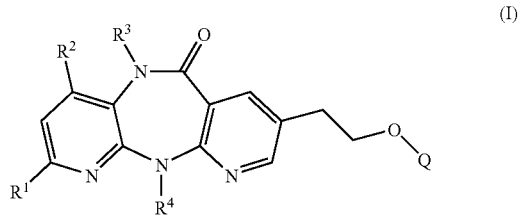

(I)

wherein
R$^1$ is selected from the group consisting of H, halogen, (C$_{1-4}$)alkyl, O(C$_{1-6}$)alkyl, and haloalkyl;
R$_2$ is H or (C$_{1-4}$)alkyl;
R$^3$ is H or (C$_{1-4}$)alkyl;
R$^4$ is (C$_{1-4}$)alkyl, (C$_{1-4}$)alkyl(C$_{3-7}$)cycloalkyl, or (C$_{3-7}$)cycloalkyl; and
Q is a fused phenyl-5 or 6-membered saturated heterocycle having one or two heteroatoms selected from O and N, said Q is selected from the group consisting of:
a)

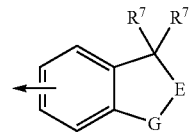

wherein one of E and G is C(O) and the other is NR$^5$ wherein R$^5$ is selected from the group consisting of H, hydroxy and (C$_{1-4}$)alkyl unsubstituted or substituted with pyridinylmethyl, (pyridinyl-N-oxide)methyl or C(O)OR$^6$ wherein R$^6$ is H or (C$_{1-4}$)alkyl; and each R$^7$ is independently H, Me or Et; or b)

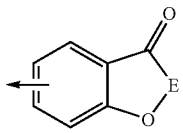

wherein E is NR$^8$ wherein R$^8$ is H, (C$_{1-4}$)alkyl unsubstituted or substituted with C(O)OR$^9$ wherein R$^9$ is H or (C$_{1-4}$)alkyl; or c)

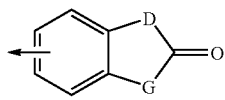

wherein D and G are NR$^{10}$ wherein each R$^{10}$ is independently H or (C$_{1-4}$)alkyl unsubstituted or substituted with C(O)OR$^{11}$ wherein R$^{11}$ is H or (C$_{1-4}$)alkyl; or d)

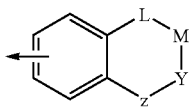

wherein one of L, M, Y and Z is NR$^{12}$ wherein R$^{12}$ is H, (C$_{1-4}$)alkyl unsubstituted or substituted with C(O)OR$^{12x}$ wherein R$^{12x}$ is H or (C$_{1-4}$)alkyl; one of the remaining positions of L, M, Y and Z adjoining the NR$^{12}$ is C(O); and the remaining two positions are each CR$^{13}$R$^{13}$ wherein each R$^{13}$ is independently H, Me or Et; or e)

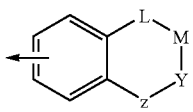

wherein three adjoining positions of L, M, Y and Z (namely L-M-Y or M-Y-Z) represent NR$^{14}$—C(O)—O— or —NR$^{15}$—C(O)—NR$^{16}$— wherein R$^{14}$, R$^{15}$ and R$^{16}$ each represents H or (C$_{1-4}$)alkyl unsubstituted or substituted with C(O)OR$^{17}$ wherein R$^{17}$ is H or (C$_{1-4}$)alkyl; and the remaining position of L, or Z is CR$^{18}$R$^{18}$ wherein each R$^{18}$ is H, Me or Et;

or a pharmaceutically acceptable salt, or prodrug thereof.

According to a second aspect of the invention, there is provided a pharmaceutical composition for the treatment or prevention of HIV infection, comprising a compound of formula I, as described herein, or a pharmaceutically acceptable salt, ester or prodrug thereof, and a pharmaceutically acceptable carrier.

According to a third aspect of the invention, there is provided a method for the treatment or prevention of HIV infection, comprising administering to a patient an HIV inhibiting amount of a compound of formula I as described herein, or a pharmaceutically acceptable salt, ester or prodrug thereof.

According to a fourth aspect of the invention, there is provided a method for the treatment or prevention of HIV infection, comprising administering to a patient an HIV inhibiting amount of a pharmaceutical composition, as described herein.

According to a fifth aspect of the invention, there is provided a method for treating or preventing HIV infection comprising administering a compound of formula I, as described herein, in combination with an antiretroviral drug.

According to a sixth aspect of the invention, there is provided a method for preventing perinatal transmission of HIV-1 from mother to baby, comprising administering a compound of formula I, as described herein, to the mother before giving birth.

According to a seventh embodiment of the invention, there is provided the use of a compound of formula I as defined herein, for the manufacture of a medicament for the treatment or prevention of HIV infection.

According to an eighth aspect of the invention, there is provided a process for producing a compound of formula I comprising steps of:

coupling a compound of formula II:

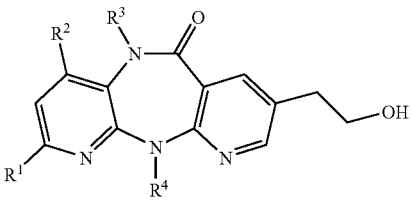

(II)

wherein R$^1$, R$^2$, R$^3$ and R$^4$ are as described herein;

with a phenolic derivative selected from:

a)

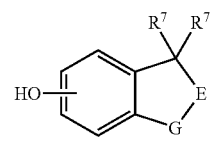

wherein one of E and G is C(O) and the other is NR$^{5A}$ wherein R$^{5A}$ is a N-protecting group, hydroxy or (C$_{1-4}$)alkyl unsubstituted or substituted with pyridylmethyl, (pyridinyl-N-oxide) methyl or C(O)OR$^{6A}$ wherein R$^{6A}$ is a carboxy protecting group or (C$_{1-4}$)alkyl; and each R$^7$ is independently H, Me or Et.

b)

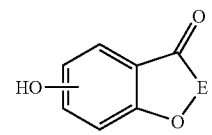

wherein E is NR$^{8A}$ wherein R$^{8A}$ is a N-protecting group, (C$_{1-4}$)alkyl unsubstituted or substituted with C(O)OR$^{9A}$ wherein R$^{9A}$ is a carboxy protecting group or (C$_{1-4}$)alkyl; or c)

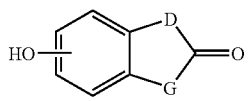

wherein D and G each independently is $NR^{10A}$ wherein $R^{10A}$ is a N-protecting group or $(C_{1-4})$alkyl unsubstituted or substituted with $C(O)OR^{11A}$ wherein $R^{11A}$ is a carboxy protecting group or $(C_{1-4})$alkyl;

d)

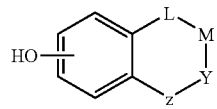

wherein one of L, M, Y and Z is $NR^{12A}$ wherein $NR^{12A}$ is a N-protecting group, $(C_{1-4})$alkyl unsubstituted or substituted with $C(O)OR^{12y}$ wherein $R^{12y}$ is a carboxy protecting group or $(C_{1-4})$alkyl; one of the remaining positions of L, M, Y and Z adjoining the $NR^{12A}$ is C(O); and the remaining two positions are each $CR^{13}R^{13}$ wherein each $R^{13}$ is independently H, Me or Et; or e)

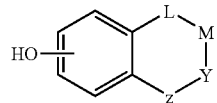

wherein three adjoining positions of L, M, Y and Z (namely L-M-Y or M-Y-Z) represent —$NR^{14}$—C(O)—O— or —$NR^{15}$—C(O)—$NR^{16}$— wherein $R^{14}$, $R^{15}$ and $R^{16}$ are as defined hereinbefore, and the remaining position of L or Z is $CR^{18}R^{18}$ wherein each $R^{18}$ is as defined hereinbefore;

and, if required, removing any protective groups in a mixture of aqueous base or aqueous acid in a co-solvent, to obtain the corresponding compound of formula I.

According to a ninth aspect of this invention, there is provided a pharmaceutical preparation for use in the treatment or prevention of HIV infection, wherein the active ingredient is a compound of formula 1 as defined herein, or a pharmaceutically acceptable salt, ester or prodrug thereof.

DETAILED DESCRIPTION OF THE INVENTION

Definitions

The following definitions apply unless otherwise noted:

As used herein, the term "carboxy protecting group" means a group capable of protecting a carboxy against undesirable reactions during synthetic procedures (see "Protective Groups in Organic Synthesis", Theodora W. Greene and Peter G. M. Wuts, third edition, 1999). For example, carboxy protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

As used herein, the term "$(C_{1-4})$alkyl", either alone or in combination with another radical, is intended to mean acyclic straight or branched chain alkyl radicals containing from one to four carbon atoms respectively. Examples of such radicals include methyl, ethyl, propyl, isopropyl, butyl, sec-butyl, and tert-butyl.

As used herein, the term "$(C_{3-7})$cycloalkyl" is intended to mean saturated cyclic hydrocarbon radicals containing from three to seven carbon atoms and includes cyclopropyl, cyclobutyl, cyclopentyl, cyclohexyl, and cycloheptyl.

The term "haloalkyl" as used herein, either alone or in combination with another substituent, means acyclic, straight or branched chain alkyl substituents having one or more hydrogens substituted for a halogen selected from bromo, chloro, fluoro or iodo.

The term "$\{(C_{1-6})$alkyl-$(C_{3-7})$cycloalkyl$\}$" as used herein means a cycloalkyl radical containing from 3 to 6 carbon atoms directly linked to an alkylene radical containing 1 to 7 carbon atoms; for example, cyclopropylmethyl, cyclopentylethyl, cyclohexylmethyl, and cyclohexylethyl.

As used herein, the term "fused phenyl-5 or 6-membered saturated heterocycle," either alone or in combination with another radical, is intended to mean a phenyl that is fused with a 5 or 6-membered non-aromatic heterocycle having from 1 to 2 heteroatoms selected from oxygen and nitrogen. Examples include 1,2-dihydro-1H-benzimidazole and 1,2,3,4-tetrahydroisoquinoline.

As used herein, the term "inhibitor of HIV replication" means that the ability of HIV-1 reverse transcriptase to replicate a DNA copy from an RNA template is substantially reduced or essentially eliminated.

The terms "nitrogen protecting group" or "N-protecting group" as used herein interchangeably, means a group capable of protecting a nitrogen atom against undesirable reactions during synthetic procedures (see "Protective Groups in Organic Synthesis", Theodora W. Greene and Peter G. M. Wuts, third edition, 1999). N-protecting groups include, for example: Alkyl carbamates (such as methyl, ethyl or t-butyl) and aryl carbamates (such as benzyl).

As used herein, the term "pharmaceutically acceptable salt" includes those derived from pharmaceutically acceptable bases and is non-toxic. Examples of suitable bases include choline, ethanolamine and ethylenediamine. $Na^+$, $K^+$, and $Ca^{++}$ salts are also contemplated to be within the scope of the invention (also see Pharmaceutical salts, Birge, S. M. et al., J. Pharm. Sci., (1977), 66, 1–19, incorporated herein by reference).

As used herein, the term "prevention" means the administration of a compound or composition according to the present invention post-exposure of the individual to the virus but before the appearance of symptoms of the disease, and/or prior to the detection of the virus in the blood.

As used herein, the term "prodrug" refers to pharmacologically acceptable derivatives, such that the resulting biotransformation product of the derivative is the active drug, as defined in compounds of formula I. Examples of such derivatives include, but are not limited to, esters and amides. (see Goodman and Gilman in The Pharmacological Basis of Therapeutics, 9th ed., McGraw-Hill, Int. Ed. 1995, "Biotransformation of Drugs, p 11–16, incorporated herein by reference).

As used herein, the term "single or double mutant strains" means that either one or two amino acid residues that are present in WT HIV-1 strain have been replaced by residues not found in the WT strain. For example, the single mutant Y181C is prepared by site-directed mutagenesis in which the tyrosine at residue 181 has been replaced by a cysteine residue. Similarly, for the double mutant K103N/Y181C, an asparagine residue has replaced the lysine at residue 103 and a cysteine residue has replaced the tyrosine at residue 181.

Preferred Embodiments

Preferably, compounds are of formula I as defined above, wherein $R^1$ is selected from: H, Cl, F, $(C_{1-4})$alkyl and $CF_3$. More preferably, $R^1$ is H, Cl, F or Me.

Preferably, $R^2$ and $R^3$ is each independently H or Me. More preferably $R^2$ is H and $R^3$ is Me.

Preferably, $R^4$ is ethyl or cyclopropyl. More preferably, $R^4$ is ethyl.

Preferably, Q is

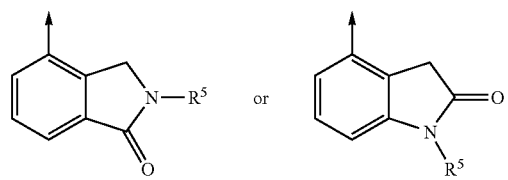

wherein $R^5$ is H, hydroxy, $CH_3$ or (4-pyridinyl)methyl.

More preferably, Q is

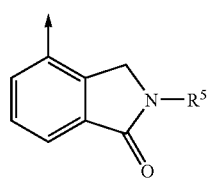

wherein $R^5$ is H, hydroxy or (4-pyridinyl)methyl.

Most preferably, Q is

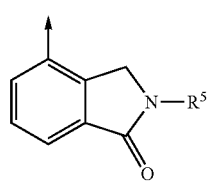

wherein $R^5$ is H or hydroxy.

Preferably, Q is

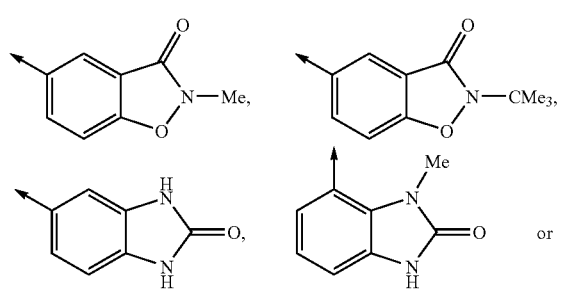

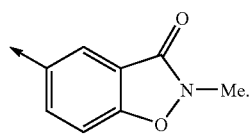

More preferably, Q is

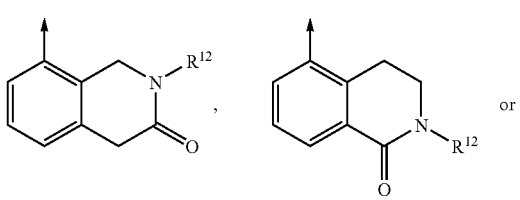

Preferably, Q is

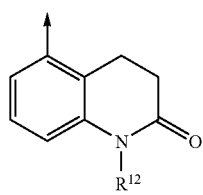

wherein $R^{12}$ is H, Me or $CH_2C(O)OH$.

More preferably, Q is

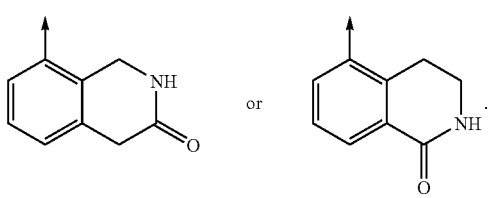

Most preferably, Q is

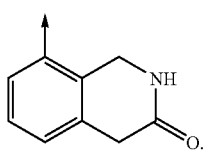

Preferably, Q is

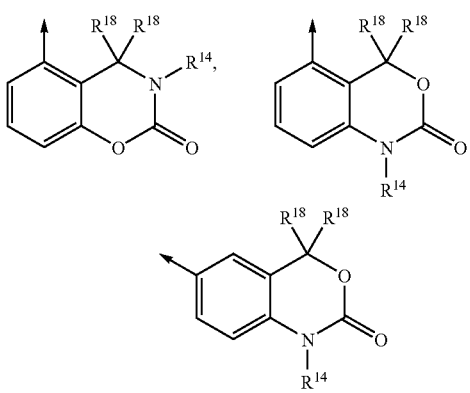

wherein $R^{14}$ is H, Me or $CH_2C(O)OH$ and each $R^{18}$ is independently H or Me. More preferably, $R^{14}$ is H or $CH_2C(O)OH$ and each $R^{18}$ is H.

Most preferably, Q is

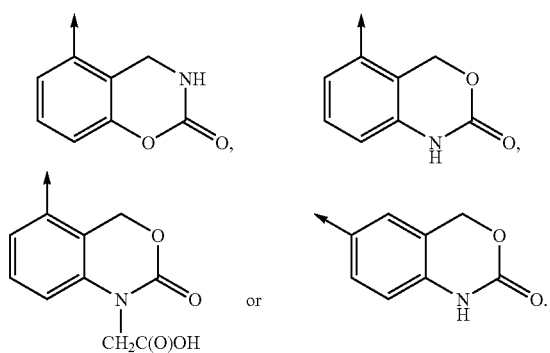

Preferably, Q is

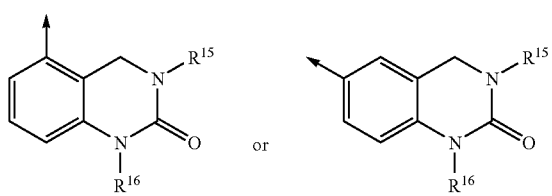

wherein $R^{15}$ is H, Me or $CH_2C(O)OH$ and $R^{16}$ is H, Me or $CH_2C(O)OH$. More preferably, $R^{15}$ is H or $CH_3$ and $R^{16}$ is H, $CH_3$ or $CH_2C(O)OH$.

Most preferably, Q is

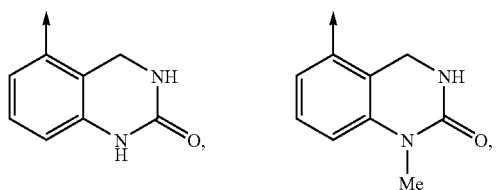

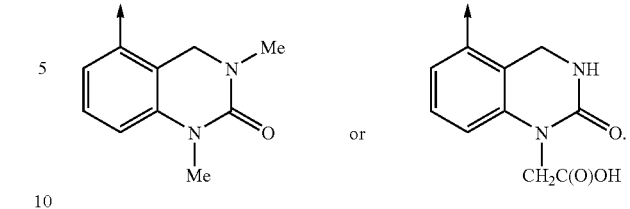

Still most preferably, $R^1$ is H, $R^2$ is H, $R^3$ is Me, $R^4$ is ethyl and Q is selected from:

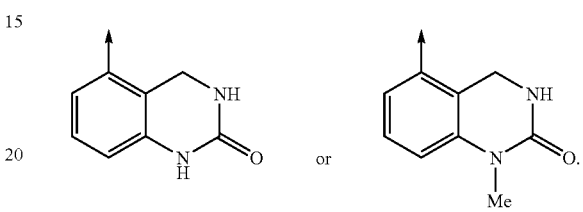

Specific Embodiments

Included within the scope of this invention are all compounds of Formula I as presented in Table 1.

Antiviral Activity

The compounds of formula I are effective inhibitors of wild type HIV as well as inhibiting the double mutation enzyme K103N/Y181C. The compounds of the invention may also inhibit the single mutation enzymes V106A, Y188L, K103N, Y181C, P236L and G190A. The compounds may also inhibit other double mutation enzymes including K103N/P225H, K103N/V108I and K103N/L100I.

The compounds of formula I possess inhibitory activity against HIV-1 replication. When administered in suitable dosage forms, they are useful in the treatment of AIDS, ARC and related disorders associated with HIV-1 infection. Another aspect of the invention, therefore, is a method for treating HIV-1 infection which comprises administering to a human being, infected by HIV-1, a therapeutically effective amount of a novel compound of formula I, as described above. Whether it is termed treatment or prophylaxis, the compounds may also be used to prevent perinatal transmission of HIV-1 from mother to baby, by administration to the mother before giving birth.

The compounds of formula I may be administered in single or divided doses by the oral, parenteral or topical routes. A suitable oral dosage for a compound of formula I would be in the range of about 0.5 mg to 3 g per day. A preferred oral dosage for a compound of formula I would be in the range of about 100 mg to 800 mg per day for a patient weighing 70 kg. In parenteral formulations, a suitable dosage unit may contain from 0.1 to 250 mg of said compounds, preferably 1 mg to 200 mg, whereas for topical administration, formulations containing 0.01 to 1% active ingredient are preferred. It should be understood, however, that the dosage administration from patient to patient would vary. The dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations that contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The compounds of formula I can be used in combination with an antiretroviral drug known to one skilled in the art, as a combined preparation useful for simultaneous, separate or sequential administration for treating or preventing HIV infection in an individual. Examples of antiretroviral drugs that may be used in combination therapy with compounds of formula I, include but are not limited to, nucleoside/nucleotide reverse transcriptase inhibitors (such as AZT and Tenofovir), non-nucleoside reverse transcriptase inhibitors (such as Nevirapine), protease inhibitors (such as Ritonavir), viral fusion inhibitors (such as T-20), CCR5 antagonists (such as SCH-351125), CXCR4 antagonists (such as AMD-3100), integrase inhibitors (such as L-870,810), TAT inhibitors, other investigational drugs (such as PRO-542, BMS-806, TMC-114 or AI-183), antifungal or antibacterial agents (such as fluconazole), and immunomodulating agents (such as Levamisole). Moreover, a compound of formula I can be used with another compound of formula I.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention may be administerable by suppository.

Methodology and Synthesis

Exemplary reaction schemes, disclosed in WO 01/96338A1, the contents of which are incorporated herein by reference, show the many synthetic routes to the tricyclic compounds 1 illustrated hereinafter. The compounds of the present invention may be made using the skills of a synthetic organic chemist. An exemplary reaction scheme is illustrated in Scheme 1. Substituents $R^1$, $R^2$, $R^3$, $R^4$, and Q are as defined herein. Q' is a Q derivative that can be converted to Q by art recognized chemistry.

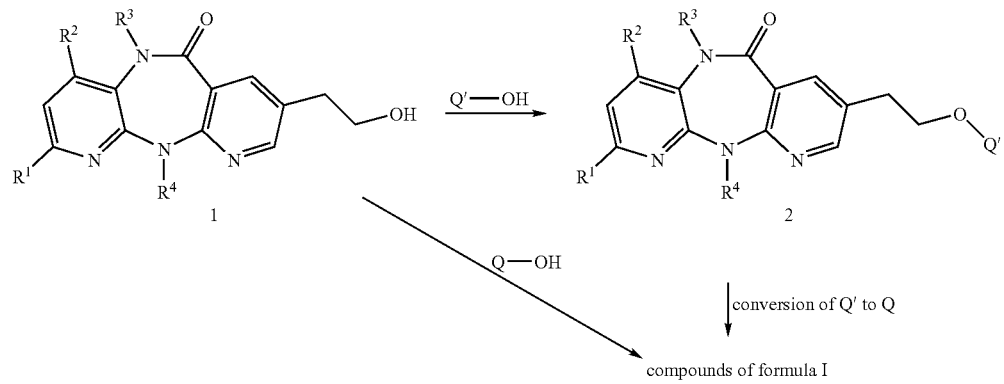

Using a Mitsunobu-type reaction, phenolic derivatives Q-OH are condensed with 1 to produce compounds of formula I. Alternatively, phenolic derivatives Q'-OH can also be condensed with 1 to give intermediate 2. Intermediate 2 can be converted to compounds of formula I by art-recognized chemistry (e.g. removal of protective groups, alkylation, oxidation or functional group modification to convert Q' to Q). Phenolic derivatives Q-OH and Q'-OH are readily available or can easily be prepared by those skill in the art using standard methods. Other methods of condensation to produce the ether linkage in compounds of formula I are also contemplated, for example a $S_N2$ displacement of a suitably derivatized primary alcohol in 1 by Q-OH or Q'-OH.

As stated before, the compounds provided by the invention inhibit the enzymatic activity of HIV-1 RT. Based upon testing of these compounds, as described below, it is known that they inhibit the RNA-dependent DNA polymerase activity of HIV-1 RT. Utilizing the Reverse Transcriptase (RT) Assay described below, compounds can be tested for their ability to inhibit the RNA-dependent DNA polymerase activity of HIV-1 RT. Certain specific compounds described in the Examples which appear below, were so tested. The results of this testing appear in Table 2 as $IC_{50}$ (nM) and $EC_{50}$ (nM).

EXAMPLES

The present invention is illustrated in further detail by the following non-limiting examples. All reactions were performed in a nitrogen or argon atmosphere unless otherwise stated. Temperatures are given in degrees Celsius. Solution percentages or ratios express a volume to volume relationship, unless stated otherwise.

Abbreviations or symbols used herein include:

DEAD: diethyl azodicarboxylate;
DIAD: diisopropyl azodicarboxylate;
DMSO: dimethylsulfoxide;
DMF: dimethylformamide;
ES MS: electron spray mass spectrometry;
Et: ethyl;
EtOH: ethanol;
EtOAc: ethyl acetate;
$Et_2O$: diethyl ether;
HPLC: high performance liquid chromatography;
iPr: isopropyl;
Me: methyl;
MeOH: methanol;
MeCN: acetonitrile;
NaHMDS; sodium hexamethyldisilazide
NBS: N-bromosuccinimide;
Ph: phenyl;
TFA: trifluoroacetic acid;
THF: tetrahydrofuran;

Syntheses

The following examples illustrate methods for preparing compounds of the invention

Example 1

5,11-Dihydro-11-ethyl-8-(2-hydroxyethyl)-5-methyl-6H-dipyrido[3,2-b:2',3'-e][1,4]diazepin-6-one Step a:
To a solution of 2-chloro-3-nitropyridine 1a (51 g, 325 mmol) in THF (650 mL) was added a 2 M solution of ethylamine in THF (365 mL, 731 mmol). The reaction was stirred at room temperature overnight. The reaction mixture was poured into water (~1.5 L) and the resulting solid was filtered and dried under reduced pressure to give compound 1b (52 g).

Step b:
A solution of 2-(ethylamino)-3-nitropyridine 1b (52 g) in MeOH (600 mL) was stirred overnight at room temperature under hydrogen (1 atm.) in the presence of 20% $Pd(OH)_2$/C (10.4 g). The catalyst was removed by filtration through diatomaceous earth. The filtrate was concentrated under reduced pressure to give compound 1c as a black solid (39 g, 88% yield over steps a) and b).

Step c:

To a cooled solution of 3-amino-2-(ethylamino)pyridine 1c (30.6 g, 223 mmol) in MeCN (740 mL) was added solid NaHCO$_3$ (56.3 g, 669 mmol). After 5 min, crude 5-bromo-2-chloro-3-pyridinecarbonyl chloride (prepared from 5-bromo-2-hydroxy-3-pyridinecarboxylic acid and SOCl$_2$ [as described by T. W. Gero et al. in Synth. Commun. 1989, 19, 553–559 (incorporated herein by reference) but with omission of the aqueous work-up] was added (1 equiv., 223 mmol). After 2 h, the reaction mixture was poured over ice/H$_2$O (1.5 L) and the resulting solid was filtered, rinsed with H$_2$O and then hexane. After drying under reduced pressure overnight, compound 1d was obtained as a black solid (54.9 g, 69% yield).

Step d:

To a solution of 2-chloro-N-{2-(ethylamino)-3-pyridinyl}-5-bromo-3-pyridinecarboxamide 1d (54.9 g, 154.4 mmol) in pyridine (308 mL) at 50° C. was added dropwise a 1.0 M solution of NaHMDS in THF (355 mL, 355 mmol). After 10 min, the reaction was allowed to cool to room temperature, and then was poured over ice water (2 L). The resulting solid was filtered, rinsed with water and then hexane. The solid was dried under reduced pressure to give compound 1e (36 g, 75% yield) as a dark green solid.

Step e:

To a solution of the 8-bromo-5,11-dihydro-11-ethyl-6H-dipyrido[3,2-b:2',3'-e][1,4]diazepin-6-one 1e (36.7 g, 115 mmol) in DMF (380 mL) was added NaH (3.5 g, 138 mmol), and the mixture was heated to 50° C. for 30 min. The reaction mixture was cooled to room temperature and treated with MeI (14.3 mL, 230 mmol). After 1.5 h, the reaction mixture was poured over ice water. The solid was filtered, washed with water and then hexane to give after drying, compound 1f (37.9 g, 99% yield) as a dark grey solid.

Step f:

Allyltributyltin (30.7 mL, 99.0 mmol) and Pd(Ph$_3$P)$_4$ (5.20 g, 4.50 mmol) were added to a degassed (N$_2$ through solution for 30 min) solution of 8-bromo-5,11-dihydro-11-ethyl-5-methyl-6H-dipyrido[3,2-b:2',3'-][1,4]diazepin-6-one 1f (30.0 g, 90.0 mmol) in was cooled to room temperature and concentrated under reduced pressure. The residue was purified by flash chromatography (hexane: EtOAc, 8/2 to 7/3) to give compound 1 g (22.2 g, 84% yield).

Step g:

A stream of ozonized oxygen was bubbled through a cold (−78° C.) solution of 5,11-dihydro-11-ethyl-5-methyl-8-(2-propenyl)-6H-dipyrido[3,2-b:2',3'-e][1,4]diazepin-6-one 1g (22.19 g, 75.4 mmol) in CH$_2$Cl$_2$ (150 mL) and MeOH (150 mL) for 2.5 h. A stream of N$_2$ was next bubbled through the solution for 15 min and then solid NaBH$_4$ (4.99 g, 132 mmol) was added to the solution. The reaction mixture was allowed to warm to room temperature. After 1 h, aqueous saturated NH$_4$Cl (200 mL) was added and the mixture was stirred at room temperature for 2 h. The organic solvents were removed under reduced pressure. Water (300 mL) and CHCl$_3$ (300 mL) were added to the residue. The phases were separated and the aqueous layer was extracted with CHCl$_3$ (3×300 mL). The combined organic layers were dried (MgSO$_4$), filtered and concentrated under reduced pressure. The residue was purified by flash chromatography (EtOAc/CHCl$_3$, 4/1) to give compound 1 h (16.1 g, 72% yield) as a white solid.

Example 2

Entries 101 and 104

5,11-Dihydro-8-{2-{(2,3-dihydro-1-oxo-1H-isoindol-4-yl)oxy}ethyl}-11-ethyl-5-methyl-6H-dipyrido[3,2-b:2',3'-e][1,4]diazepin-6-one and 5,11-dihydro-8-{2-{{2,3-dihydro-1-oxo-2-(4-pyridinylmethyl)-1H-isoindol-4-yl}oxy}ethyl}-11-ethyl-5-methyl-6H-dipyrido[3,2-b:2',3'-e][1,4]diazepin-6-one

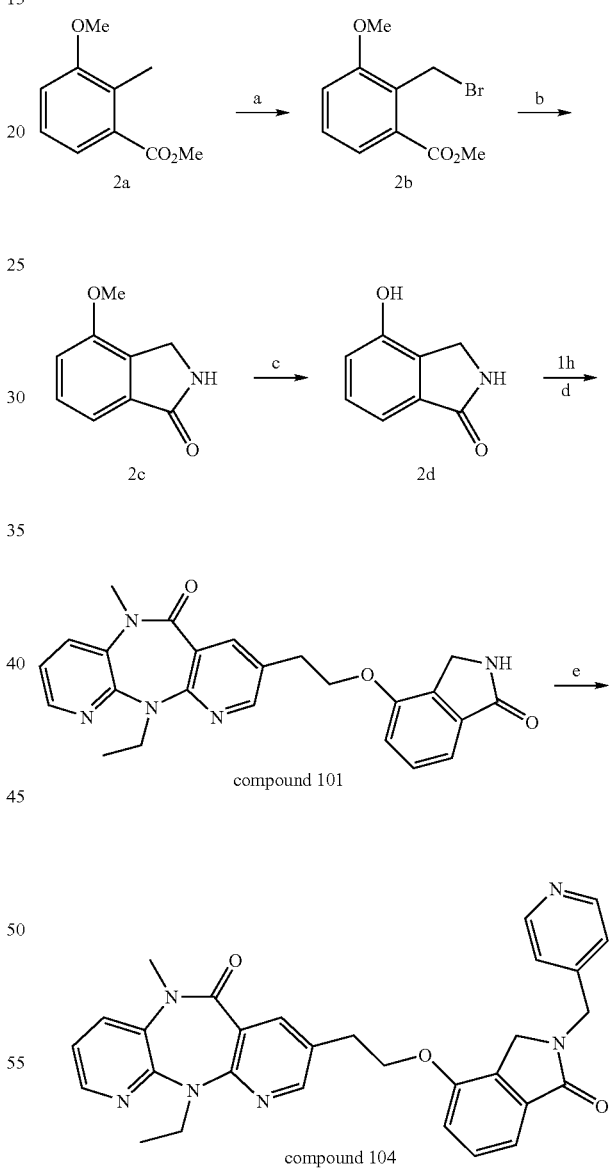

Step a:

A solution of 2a (2.58 g, 14.3 mmol), NBS (2.79 g, 15.7 mmol) and AIBN (232 mg, 1.41 mmol) in CCl$_4$ (20 mL) was refluxed for 3 h. The reaction mixture was cooled to room temperature and the resulting suspension was filtered. The filtrate was concentrated under reduced pressure and the residue was purified by flash chromatography (hexane/CH$_2$Cl$_2$, 75/25) to give 2b (3.4 g, 92% yield) as a white solid.

Step b:

A solution of 2b (997 mg, 3.85 mmol) in THF (19 mL) and ammonium hydroxide (9 mL) was stirred at room temperature for 4 h. The reaction mixture was evaporated to dryness. The residue was purified by flash chromatography (hexane/EtOAC, 40/60, containing MeOH 1%) to give 2c as a white solid (595 mg, 95% yield).

Step c:

To an ice-cold solution of 2c (291 mg, 1.78 mmol) in CH$_2$Cl$_2$ (20 mL) was added a 1.0 M BBr$_3$ solution in CH$_2$Cl$_2$ (3.6 mL, 3.6 mmol). The cold bath was then removed and the resulting solution was stirred for 16 h at ambient temperature. The reaction was carefully quenched by addition of water and the mixture was extracted with EtOAc. The combined organic layers were washed with water and brine, dried (MgSO$_4$), filtered and evaporated to dryness to give 2d (232 mg, 87% yield) as beige solid.

Step d:

A solution of DEAD (250 µL, 1.59 mmol) in THF (1 mL) was added dropwise to a solution of 1 h (50.6 mg, 0.17 mmol), Ph$_3$P (54.5 mg, 0.21 mmol) and phenol 2d (24.9 mg, 0.17 mmol) in THF (1.8 mL) at room temperature. After 16 h, the mixture was concentrated under reduced pressure and the residue was purified by flash chromatography (EtOAc/EtOH, 92/8) to give compound 101 (20 mg, 28% yield) as a white solid.

Step e:

To an ice-cold solution of compound 101 (60 mg, 0.14 mmol) in THF/DMF (1/1, 0.7 mL) was added 1.0 M NaHMDS solution in THF (168µL, 0.17 mmol). After 15 min, a solution of 4-chloropyridine (31.8 mg, 0.28 mmol) in DMF (0.25 mL) was added and the reaction was stirred at room temperature for 5 h. The reaction mixture was quenched with water and extracted with EtOAc. The combined organic phases were washed with water and brine, dried (MgSO$_4$), filtered and evaporated under reduced pressure. The residue was purified by flash chromatography (EtOAc/MeOH, 95/5 to 90/10) to give compound 104 (45 mg, 62% yield) as a white solid.

Example 3

Entry 103

5,11-Dihydro-8-{2-{(2,3-dihydro-2-hydroxy-1-oxo-1H-isoindol-4-yl)oxy}ethyl}-11-ethyl-5-methyl-6H-dipyrido[3,2-b:2',3'-e][1,4]diazepin-6-one

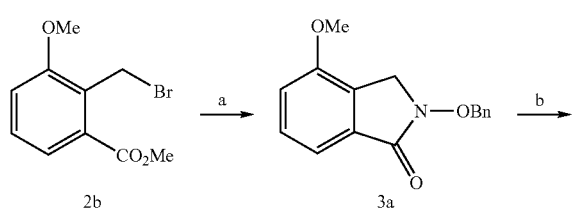

-continued

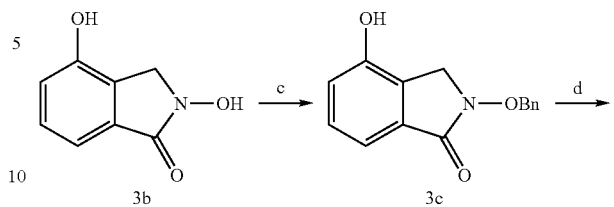

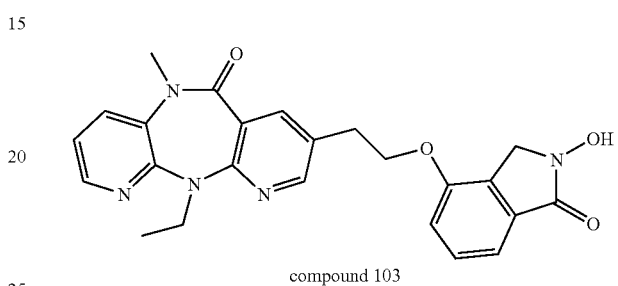

compound 103

Step a:

A solution of 2b (2.03 g, 7.83 mmol), O-benzylhydroxylamine hydrochloride (1.25 g, 7.83 mmol) and CsOH.H$_2$O (2.88 g, 17.2 mmol) in DMF (15 mL) was heated to 90° C. for 4 h. Aqueous 0.5 M HCl solution (30 mL) was added and the mixture was extracted with EtOAc. The combined organic phases were washed with water and brine, dried (MgSO$_4$), filtered and concentrated under reduced pressure. The residue was purified by flash chromatography (hexane/EtOAc, 70/30) to give 3a (481 mg, 23% yield).

Step b:

Following the procedure described for step c in Example 2, compound 3a (470 mg, 1.74 mmol) gave compound 3b (175 mg, 61% yield) as a white solid.

Step c:

A solution of DIAD (300 µL, 1.52 mmol) in THF (1 mL) was added dropwise to a solution of 3b (170 mg, 1.03 mmol), Ph$_3$P (405 mg, 1.54 mmol) and benzyl alcohol (170 mg, 1.57 mmol) in THF (1.8 mL) at room temperature. The mixture was stirred at room temperature for 2 h then was concentrated under reduced pressure. The residue was purified by flash chromatography (hexane/EtOAc, 60/40) to give phenol 3c (149 mg, 57% yield).

Step d:

Following the procedure described for step c in Example 3, phenol 3c (146 mg, 0.57 mmol) and alcohol 1 h (143 mg, 0.48 mmol) gave the corresponding ether (60 mg). A mixture of this compound and 20% Pd(OH)$_2$/C (10 mg) in MeOH (15 mL) was stirred under an atmosphere of hydrogen for 4 h. The reaction mixture was filtered and concentrated under reduced pressure. The residue was purified by flash chromatography (THF/CH$_2$Cl$_2$, 75/25) to give compound 103 (43 mg, 17% yield) as a white solid.

Example 4

Entries 105, 106 and 107

5,11-Dihydro-8-{2-{(2,3-dihydro-2-oxo-1H-indol-4-yl)oxy}ethyl}-11-ethyl-5-methyl-6H-dipyrido[3,2-b:2',3'-e][1,4]diazepin-6-one, 5,11-dihydro-8-{2-{(2,3-dihydro-1,3-dimethyl-2-oxo-1H-indol-4-yl)oxy}ethyl}-11-ethyl-5-methyl-6H-dipyrido[3,2-b:2',3'-e][1,4]diazepin-6-one and 5,11-dihydro-8-{2-{(2,3-dihydro-1-methyl-2-oxo-1H-indol-4-yl)oxy}ethyl}-11-ethyl-5-methyl-6H-dipyrido[3,2-b:2',3'-e][1,4]diazepin-6-one reaction mixture was concentrated under reduced pressure and the residue was taken in Et$_2$O. The solution was washed with water and brine, dried (MgSO$_4$), filtered and evaporated to dryness. The residue was purified by flash chromatography (hexane/EtOAc, 80/20) to give 4c (1.67 g, 67% yield) as a yellow solid.

Step c:

A solution of 4c (1.7 g, 8.7 mmol) in aqueous 12 N HCl solution (25 mL) and concentrated sulfuric acid (3 mL) was heated to reflux for 1.5 h. The reaction mixture was cooled to 0° C. and water (30 mL) was added. The resulting suspension was filtered and the solid was dried to give acid 4d (1.7 g, 94% yield) as a white solid.

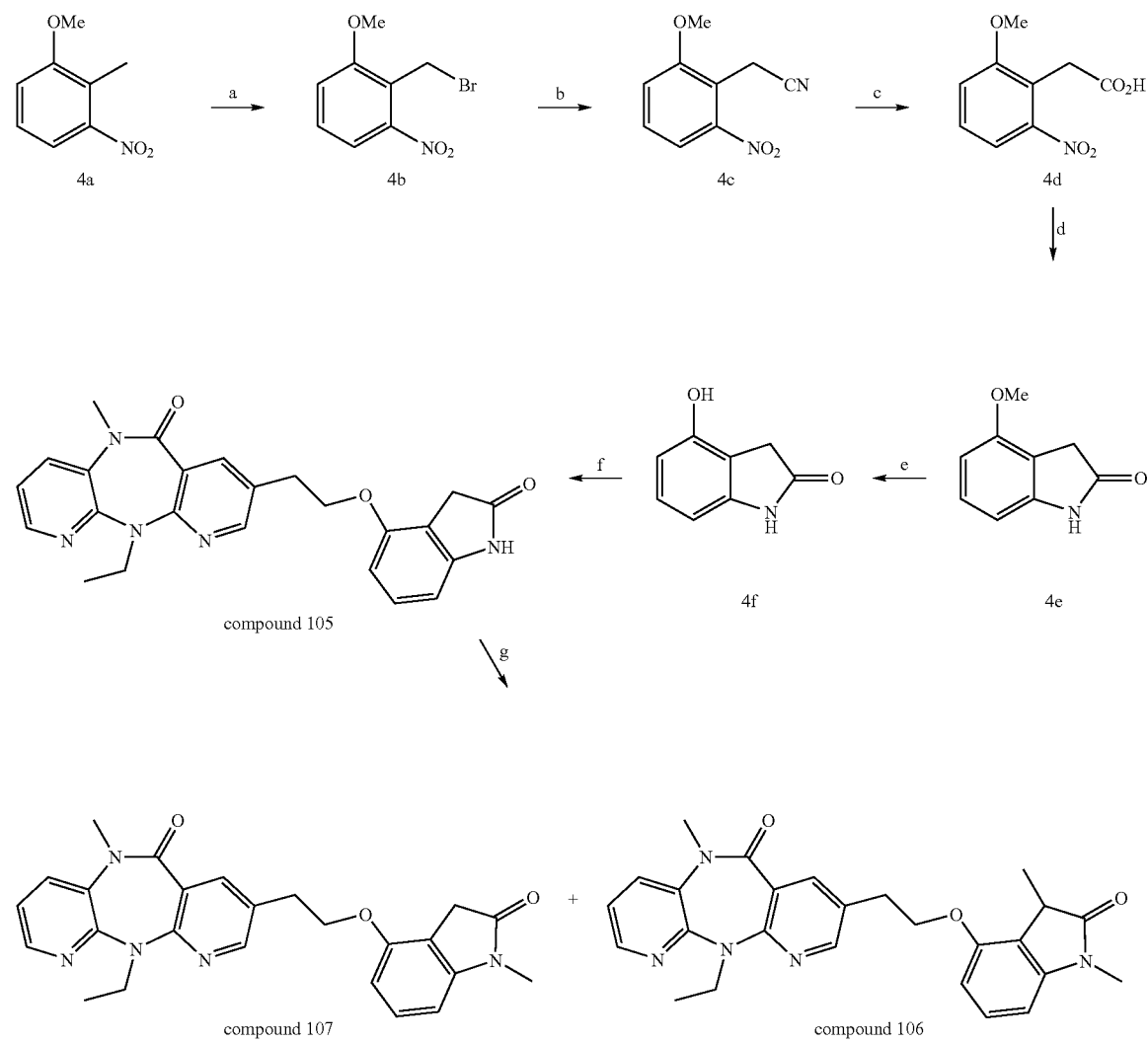

Step a:

Following the procedure described for step a in Example 2, 4 a (5.0 g, 30 mmol) gave the corresponding bromide 4b (3.2 g, 44% yield).

Step b:

A solution of 4b (3.2 9, 13 mmol) and NaCN (1.28 g, 36 mmol) in EtOH (35 mL) was heated to reflux for 4 h. The Step d:

A mixture of 4d (1.0 g, 4.7 mmol) and 10% Pd/C (70 mg) in AcOH (25 mL) was stirred under hydrogen (1 atm.) at room temperature for 16 h. The catalyst was removed by filtration through diatomaceous earth. The filtrate was concentrated under reduced pressure to give lactam 4e (766 mg, 99% yield) as a white solid.

Step e and f:

Following the procedures described for steps c and d in Example 2, 4e gave the desired compound 105 as a white solid.

Step g:

To a solution of compound 105 (22 mg, 0.05 mmol) in DMF (1 mL) were added excess $Cs_2CO_3$ and MeI. After 30 min, the reaction mixture was purified by HPLC using a gradient of $MeCN/H_2O$ containing TFA (0.06%) (Combi-Prep ODS-AQ 50×20 mm, 5μ, 120 Å) to give compound 106 (5.8 mg, 25% yield) as a white solid and compound 107 (2.8 mg, 12% yield) as a white solid.

Example 5

Entry 110

5,11-Dihydro-11-ethyl-5-methyl-8-{2-{(1,2,3,4-tetrahydro-2-oxo-5-quinazolinyl)oxy}ethyl}-6H-dipyrido[3,2-b:2',3'-e][1,4]diazepin-6-one

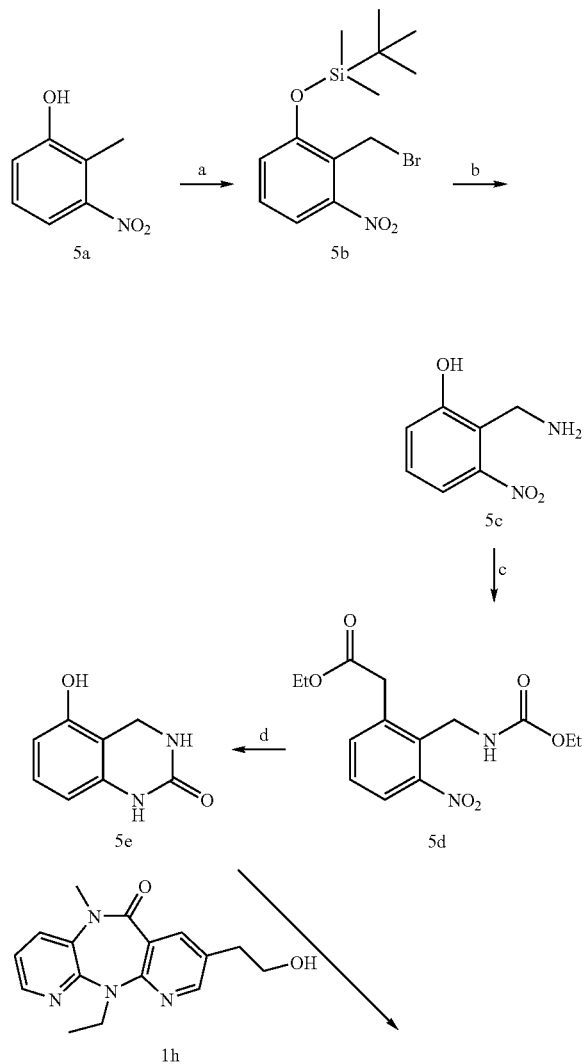

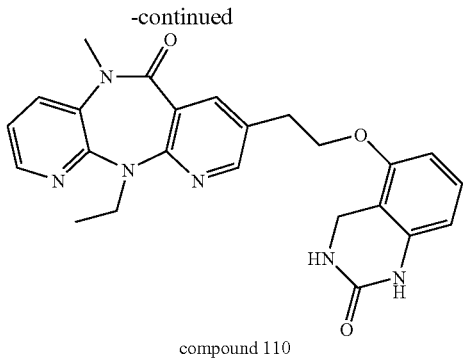

compound 110

Step a:

A solution of 5a (10.0 g, 65.3 mmol), imidazole (5.8 g, 85 mmol) and tert-butyldimethylsilyl chloride (10.8 g, 71.8 mmol) in THF (300 mL) was stirred at room temperature overnight. The mixture was diluted with EtOAc and was washed successively with water and brine, dried ($MgSO_4$), filtered and concentrated under reduced pressure. The residue was filtered through a thin pad of silica gel (hexane/$Et_2O$). A solution of the resulting yellow oil (13.3 g), AIBN (350 mg, 2.13 mmol) and NBS (10.2 g, 57.3 mmol) in $CCl_4$ (250 mL) was irradiated using a sun lamp (275 W) for 3 h. The reaction mixture was diluted with $Et_2O$, filtered through a thin pad of silica gel and concentrated under reduced pressure. The residue was purified by flash chromatography (hexane/EtOAc, 9/1) to give the bromide 5b (15 g, 66% yield).

Step b:

A solution of $NaN_3$ (7.7 g, 118 mmol) in water (10 mL) was added to a solution of 5b (8.0 g, 23.1 mmol) in THF (100 mL). After 2 h at room temperature, the reaction mixture diluted with EtOAc was washed successively with water and brine, dried ($MgSO_4$), filtered and concentrated under reduced pressure. A solution of the resulting solid and $PPh_3$ (7.7 g, 29.3 mmol) in THF (100 mL) and water (1.5 mL) was stirred at room temperature for 16 h. The reaction mixture was diluted with EtOAc and the resulting solution was washed successively with water and brine, dried ($MgSO_4$), filtered and concentrated under reduced pressure. The residue was purified by flash chromatography (EtOAc/MeOH, 9/1, then 8/2) to give 5c (2.6 g, 67% yield) as a yellow solid.

Step c:

$Et_3N$ (4.4 mL, 31.3 mmol) and ethyl chloroformate (6.0 mL, 62.5 mmol) were added to a solution of 5c (2.1 g, 12.5 mmol) in THF (150 mL). After 1 h at room temperature, the reaction mixture diluted with EtOAc was washed successively with water and brine, dried ($MgSO_4$), filtered and concentrated under reduced pressure. The residue was purified by flash chromatography (hexane/EtOAc, 5/5) to give 5d (2.96 g, 76% yield) as a white solid.

Step d:

A mixture of 5d (3.6 g, 11.5 mmol) and 10% Pd/C (360 mg) in THF (100 mL) was stirred under hydrogen (1 atm.) for 4 h. The catalyst was removed by filtration through diatomaceous earth. The filtrate was concentrated under reduced pressure. To the residue dissolved in THF (150 mL) was added Et₃N (4.0 mL, 28.9 mmol) followed by a 20% phosgene solution in toluene (6.6 mL). After 45 min at room temperature, water was added to the reaction mixture and the mixture was extracted twice with EtOAc. The combined organic layers were washed with aqueous 1 N HCl solution and brine, dried (MgSO₄), filtered and concentrated under reduced pressure to give the protected cyclic urea (3.52 g, 99%) as a yellow solid. A solution of the protected cyclic urea (2.9 g, 9.4 mmol) and aqueous 1.0 N LiOH solution (47 mL, 47 mmol) in THF (150 mL) and MeOH (50 mL) was stirred at room temperature for 1 h. The reaction mixture was acidified using aqueous 1 N HCl solution. The aqueous layer was extracted with EtOAc (4×). The combined organic layers were washed with brine, dried (MgSO₄), filtered and concentrated under reduced pressure to give compound 5e (1.5 g, 98%) as a pink solid.

Step e:

A solution of DEAD (73 μL, 0.46 mmol) in THF (0.3 mL) was added dropwise to a solution of 1 h (70 mg, 0.23 mmol), Ph₃P (122 mg, 0.46 mmol) and phenol 5e (38 mg, 0.23 mmol) in THF (8 mL) at room temperature. The reaction mixture was stirred for 16 h then was concentrated under reduced pressure. The residue was purified by flash chromatography (EtOAc) to give compound 110 (24 mg, 24% yield) as a white solid.

Example 6

Entry 122

5,11-Dihydro-8-{2-{(2,3-dihydro-2-oxo-1H-benzimidazol-5-yl)oxy}ethyl}-11-ethyl-5-methyl-6H-dipyrido[3,2-b:2',3'-e][1,4]diazepin-6-one

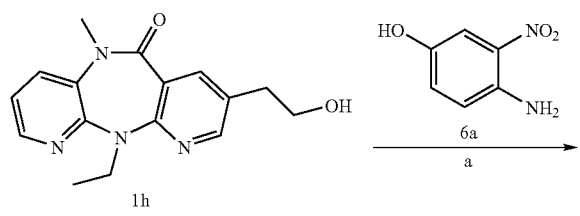

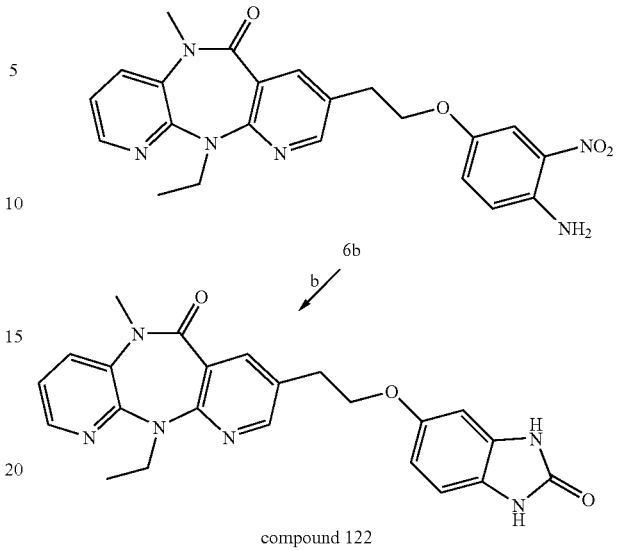

compound 122

Step a:

Following the procedure described for step d in Example 2, phenol 6a and alcohol 1 h (97.0 mg, 0.32 mmol) gave compound 6b (130 mg, 92% yield).

Step b:

A mixture of 6b (130 mg, 0.30 mmol) and 20% Pd(OH)₂/C (90 mg) in EtOH/EtOAc (1 mL/1 mL) was stirred under hydrogen (1 atm.) for 16 h at room temperature. The catalyst was removed by filtration through diatomaceous earth. The filtrate was concentrated under reduced pressure. The residue was purified by flash chromatography (CHCl₃/EtOH, 9/1) to give the corresponding phenylenediamine (82 mg. 68% yield). A 1.0 M phosgene solution in toluene (1 mL) was added to a solution of the phenylenediamine in aqueous 0.33 N HCl solution (3 mL). After 16 h at room temperature, the reaction mixture was concentrated under reduced pressure. The resulting residue was purified by preparative HPLC using a gradient of MeCN/H₂O containing TFA (0.06%) (CombiPrep ODS-AQ 50×20 mm, 5μ, 120 Å) to give compound 122 (5.8 mg, 7% yield) as a pink solid.

Example 7

Entry 123

5,11-Dihydro-11-ethyl-5-methyl-8-{2-{(1,2,3,4-tetrahydro-3-oxo-8-isoquinolinyl)oxy}ethyl}-6H-dipyrido[3,2-b:2',3'-e][1,4]diazepin-6-one

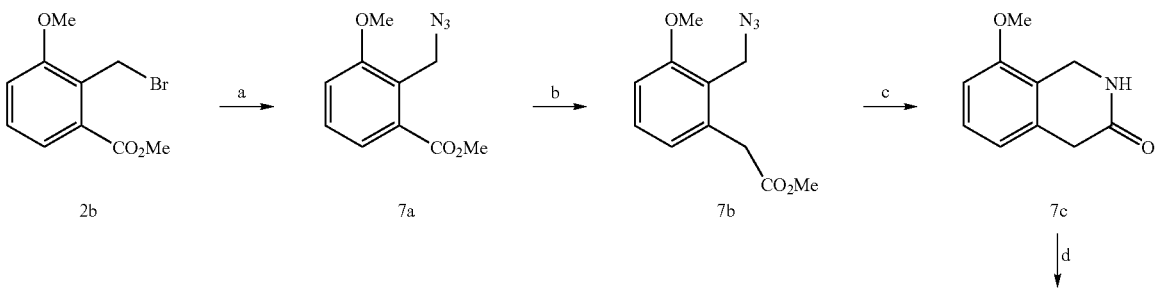

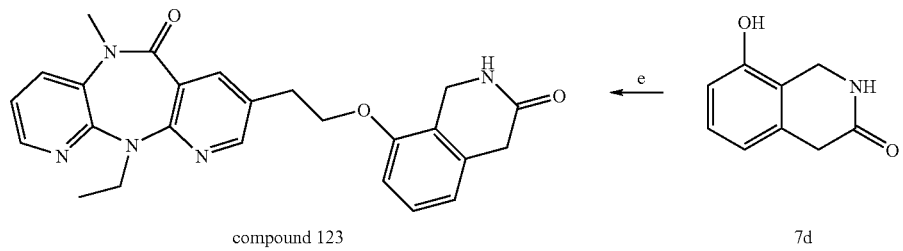

compound 123

Step a:

A solution of 2b (324 mg, 1.25 mmol) and $NaN_3$ (90 mg, 1.4 mmol) in DMF (2 mL) and $H_2O$ (1 mL) was stirred at room temperature for 1 h. The reaction mixture was diluted with $H_2O$ and extracted with EtOAc. The combined organic layers were washed with water and brine, dried ($MgSO_4$), filtered and evaporated to dryness to give 7a (260 mg, 94% yield).

Step b:

A mixture of 7a (260 mg, 1.17 mmol) and 5.0 M NaOH solution (0.9 mL, 4.50 mmol) in MeOH (1 mL) and THF (2 mL) was stirred at room temperature for 1 h. The reaction mixture was concentrated, aqueous 1 N HCl solution (10 mL) was added and the mixture was extracted with EtOAc. The combined organic layers were washed with water and brine, dried ($MgSO_4$), filtered and concentrated under reduced pressure to give the corresponding acid (235 mg, 97% yield). To a solution of the acid (235 mg, 1.1 mmol) and $Et_3N$ (175 μL, 1.25 mmol) in THF (3 mL) was added isobutyl chloroformate (160 μL, 1.25 mmol). After 10 min at room temperature, the $Et_3N \cdot HCl$ salt was filtered and rinsed with THF. To the filtrate was added excess $CH_2N_2$ solution (ca. 0.6 M, 10 mL). The reaction mixture was stirred for 2 h then was concentrated under reduced pressure to give the corresponding diazomethylketone. A mixture of the diazomethylketone, $Et_3N$ (250 μL, 1.79 mmol) and silver benzoate (10 mg, 0.04 mmol) in MeOH (5 mL) was stirred at room temperature overnight. The mixture was concentrated under reduced pressure and the residue was dissolved in EtOAc. The organic solution was washed with water and brine, dried ($MgSO_4$), filtered and concentrated under reduced pressure. The residue was purified by flash chromatography (toluene/$CH_2Cl_2$, 60/40) to give 7 b (85 mg, 32% yield).

Step c:

A solution of 7b (70 mg, 0.3 mmol) and $Ph_3P$ (100 mg, 0.38 mmol) in THF (5 mL) and $H_2O$ (0.5 mL) was stirred at room temperature for 16 h. The reaction mixture was concentrated under reduced pressure. The residue was purified by flash chromatography (hexane/EtOAc 20/80) to give 7c (41 mg, 78% yield).

Step d and e:

Following the procedure described for steps c and d in Example 2, 7c gave the desired compound 123 as a white solid.

Example 8

Entry 124

5,11-Dihydro-8-{2-{(3,4-dihydro-2-oxo-2H-1,3-benzoxazin-5-yl)oxy}ethyl}-11-ethyl-5-methyl-6H-dipyrido[3,2-b:2',3'-e][1,4]diazepin-6-one

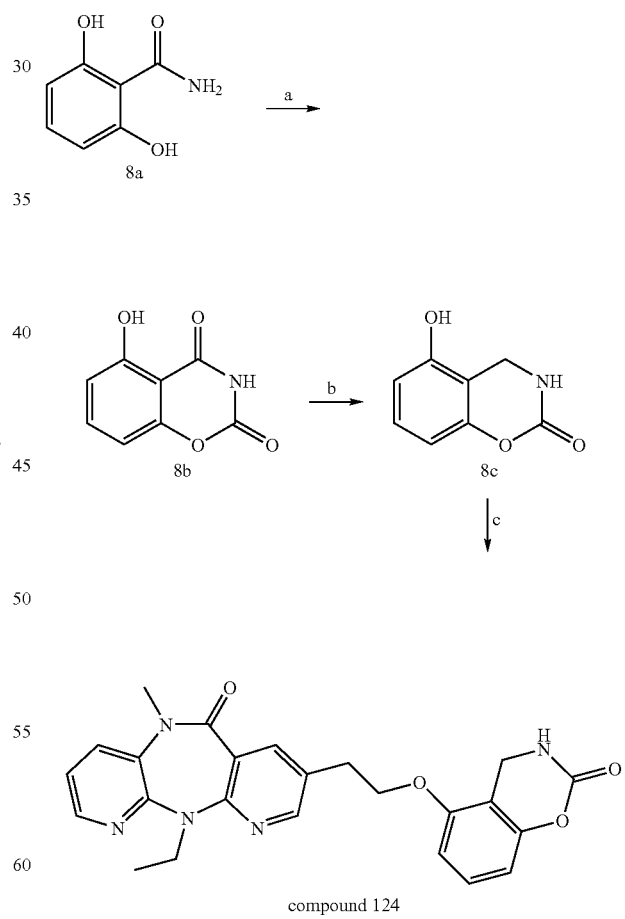

compound 124

Step a:

A solution of oxalyl chloride (0.65 mL, 7.45 mmol) in toluene (10 mL) was added dropwise to a suspension of 8a (1.0 g, 6.5 mmol) in toluene (25 mL). The reaction mixture was heated to reflux for 4 h, after which a yellow precipitate was formed upon cooling. The suspension was filtered, the solid was rinsed with toluene and dried to give 8b (1.0 g, 86% yield).

Step b:

A solution 8b (500 mg, 2.79 mmol) and 2.0 M $BH_3.Me_2S$ solution in THF (2.0 mL, 4.0 mmol) in THF (35 mL) was heated to reflux for 5 h. The reaction mixture was cooled to room temperature, MeOH (100 mL) was added and the mixture was concentrated under reduced pressure. The residue was purified by flash chromatography (hexane/EtOAc, 4/6 to 2/8) to give 8c (141 mg, 31% yield) as a white solid.

Step c:

Following the procedure described for step d in Example 2, 1h (75 mg, 0.25 mmol) and phenol 8c (42 mg, 0.25 mmol) gave compound 124 (53 mg, 47% yield) as a white solid.

Example 9

Entry 125

5,11-Dihydro-8-{2-{(1,4-dihydro-4,4-dimethyl-2-oxo-2H-3,1-benzoxazin-5-yl)oxy}ethyl}-11-ethyl-5-methyl-6H-dipyrido[3,2-b:2',3'-e][1,4]diazepin-6-one filtered and concentrated under reduced pressure. The resulting residue was treated with excess diazomethane/$Et_2O$ solution to give ester 9a (548 mg, 22% yield).

Step b:

A mixture of 9a (547 mg, 2.59 mmol) and 10% Pd/C (30 mg) in MeOH (25 mL) was stirred under hydrogen (1 atm.) for 1 h. The catalyst was removed by filtration through diatomaceous earth. The filtrate was concentrated under reduced pressure to give aniline 9b (443 mg, 94% yield).

Step c:

To a solution of 9b (170 mg, 0.94 mmol) in THF (3 mL) was added benzyl chloroformate (150 μL, 1.03 mmol) and aqueous 1.0 N HCl (1 mL). After 3 h, the reaction mixture diluted with EtOAc was washed with water and brine, dried ($MgSO_4$), filtered and concentrated under reduced pressure. The residue was purified by flash chromatography (hexane/EtOAc, 9/1) to give 9c (252 mg, 85% yield).

Step d:

To a solution of 9c (252 mg, 0.80 mmol) in THF (3 mL) was added 1.4 M methylmagnesium bromide solution in THF (3.5 mL, 4.9 mmol). The reaction mixture was stirred at room temperature for 2 h, heated to reflux for 3 h then was stirred at room temperature for 16 h. The reaction mixture was quenched with aqueous 1 N HCl solution and extracted with EtOAc. The combined organic layer was washed with

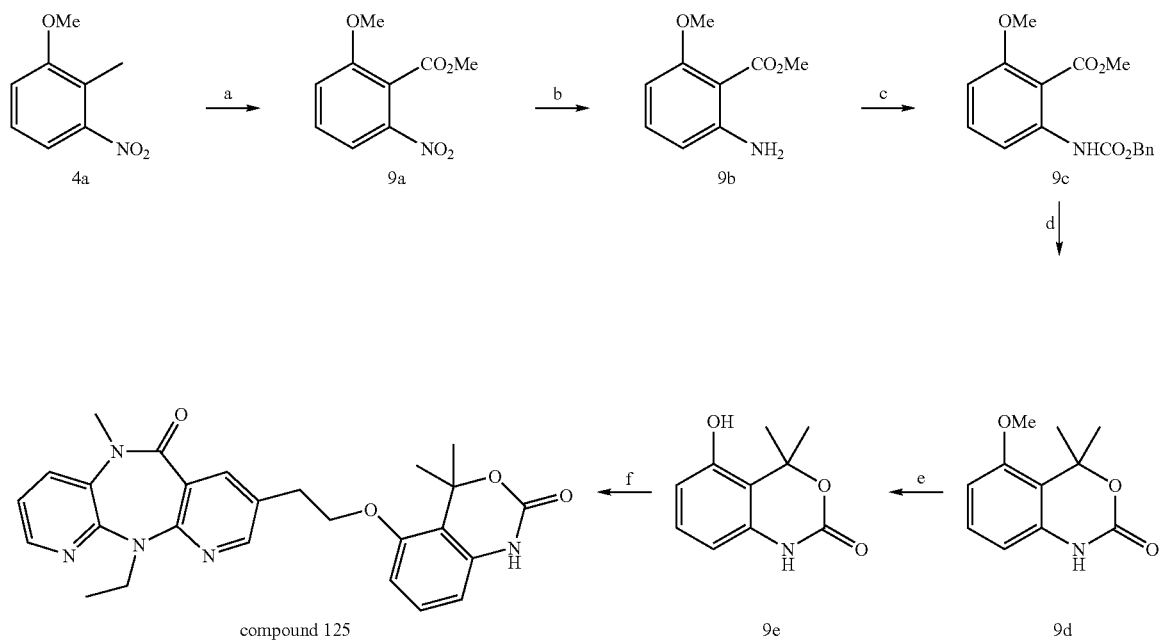

Step a:

To a suspension of 4a (2.0 g, 12 mmol) in tert-BuOH (10 mL) and water (20 mL) was added $KMnO_4$ (5.7 g, 36 mmoL). The mixture was heated to reflux for 4 h. The cooled reaction mixture was filtered through diatomaceous earth. The filtrate was acidified using aqueous 12 N HCl solution and extracted twice with EtOAc. The combined organic layer was washed with water and brine, dried ($MgSO_4$), water and brine, dried ($MgSO_4$), filtered and concentrated under reduced pressure. The residue was purified by flash chromatography (hexane/EtOAc, 8/2 to 6/4) to give 9d (94 mg, 57% yield).

Step e and f:

Following the procedure described for steps c and d in Example 2, 9d gave compound 125 as a white solid.

Example 10

Entries 126 and 128

5,11-Dihydro-8-{2-{(1,4-dihydro-2-oxo-2H-3,1-benzoxazin-5-yl)oxy}ethyl}-11-ethyl-5-methyl-6H-dipyrido[3,2-b:2',3'-e][1,4]diazepin-6-one and 5-[2-(6,11-dihydro-11-ethyl-5-methyl-6-oxo-5H-dipyrido[3,2-b:2',3'-e][1,4]diazepin-8-yl)ethoxy]-2-oxo-2H-3,1-benzoxazine-1(4H)-acetic acid

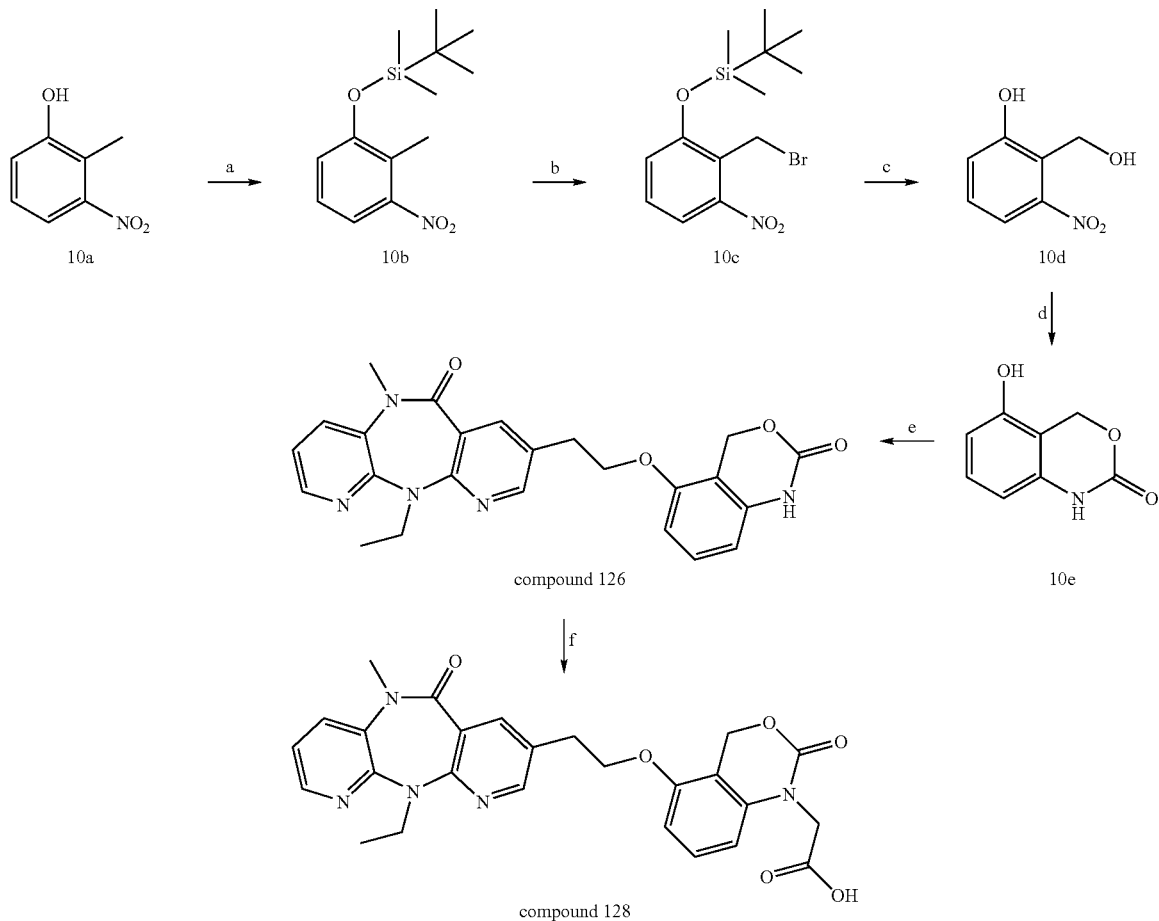

Step a:

A solution of phenol 10a (10.0 g, 65.3 mmol), imidazole (5.78 g, 84.9 mmol) and tert-butyldimethylsilyl chloride (10.8 g, 71.6 mmol) in THF (300 mL) was stirred at room temperature for 16 h. The reaction mixture was diluted with Et$_2$O and the solution was washed with water and brine, dried (MgSO$_4$), filtered and concentrated under reduced pressure. The residue was purified by flash chromatography (hexane/Et$_2$O, 4/1) to give 10b (13.3 g, 76% yield) as an oil.

Step b:

Following the procedure described for step a in Example 2, 10b (13.3 g, 49.8 mmol) gave 10c (15 g, 87% yield).

Step c:

To a solution of tert-butyldimethylsilanol (3.0 g, 22.7 mmol) in THF (100 mL) was added NaH (620 mg, 25.8 mmol). After 30 min, compound 10c (3.5 g, 10.1 mmol) was added and the reaction mixture was stirred at room temperature for 2 h. Saturated aqueous NH$_4$Cl solution was added and the mixture was extracted with Et$_2$O. The combined organic layers were washed with water and brine, dried (MgSO$_4$), filtered and concentrated under reduced pressure. The residue was purified by flash chromatography (hexane/EtOAC, 9.5/0.5) to give the desire intermediate as a gum. This compound was dissolved in 4 N HCl solution in dioxane (30 mL) and water (10 mL). After 4 h, the reaction mixture was concentrated under reduced pressure. The residue dissolved in EtOAc was washed with water and brine, dried (MgSO$_4$), filtered and concentrated under reduced pressure. The resulting residue was purified by flash chromatography (hexane/EtOAc, 1/1) to give 10d (246 mg, 14% yield).

Step d:

A mixture of 10d (2.8 g, 16.6 mmol) and 10% Pd/C (330 mg) in THF (250 mL) was stirred under hydrogen (1 atm.) for 1 h. The catalyst was removed by filtration through diatomaceous earth. The filtrate was concentrated under reduced pressure. The residue was purified by flash chromatography (hexane/EtOAc, 5/5 to 3/7) to give the corresponding aniline (273 mg, 12% yield). To a solution of this aniline (270 mg, 1.93 mmol) in THF (200 mL) was added Et$_3$N (0.62 mL, 4.45 mmol) followed by a 20% phosgene solution in toluene (1.1 mL). After 16 h, water was added to the reaction mixture and the mixture was extracted twice with EtOAc. The combined organic layers were washed with aqueous 1 N HCl solution and brine, dried (MgSO$_4$), filtered and concentrated under reduced pressure. The residue was purified by flash chromatography (hexane/EtOAc, 6/4) to give 10e (110 mg, 34% yield).

Step e:

Following the procedure described for step d in Example 2, phenol 10e gave compound 126 (55 mg, 45% yield) as a white solid.

Step f:

NaH (3.1 mg, 0.12 mmol) was added to a solution of compound 126 (38 mg, 0.08 mmol) in THF (5 mL) and DMF (1 mL). After 10 min, methyl bromoacetate (10 µL, 0.10 mmol) was added. After 1 h, the reaction mixture was diluted with EtOAc. The resulting solution was washed with aqueous 1 N HCl solution and brine, dried (MgSO$_4$), filtered and concentrated under reduced pressure. A solution of the residue and 1.0 N LiOH solution (0.1 mL) in THF (6 mL), MeOH (2 mL) and water (2 mL) was stirred at room temperature for 2 h. The reaction mixture was acidified with 1 N HCl solution and extracted with EtOAc. The organic layer was washed with water and brine, dried (MgSO$_4$), filtered and concentrated under reduced pressure. The residue was purified by reverse phase HPLC using a gradient of MeCN/H$_2$O containing TFA (0.06%) (CombiPrep ODS-AQ 50×20 mm, 5µ, 120 Å) to give compound 128 (12 mg, 28% yield) as a white solid.

Example 11

Entry 129

5,11-Dihydro-8-{2-{{2,3-dihydro-2-(1,1-dimethyl-ethyl)-3-oxo-1,2-benzisoxazol-5-yl}oxy}ethyl}-2-fluoro-11-ethyl-4-methyl-6H-dipyrido[3,2-b:2',3'-e][1,4]diazepin-6-one

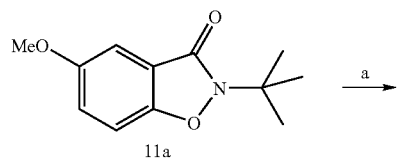

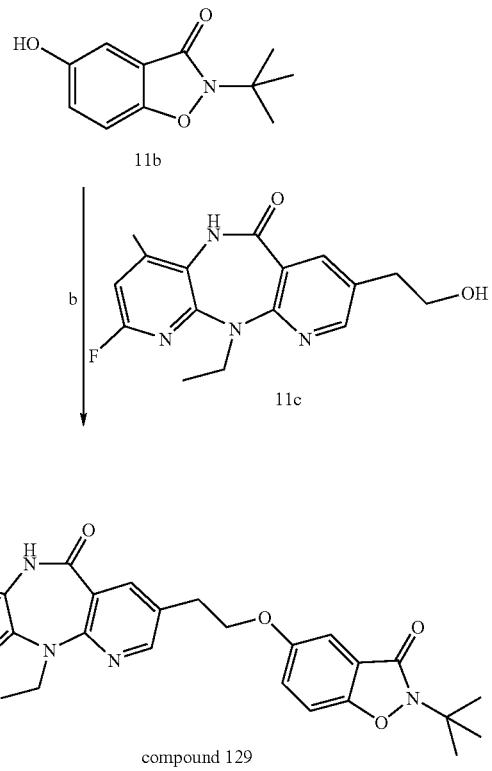

compound 129

Step a:

Following the procedure described for step c in Example 2, 11a (230 mg, 1.04 mmol) (prepared according to the procedure described in Tetrahedron Lett. 2000, 41, 2295) gave phenol 11b (155 mg 72% yield) as a pale yellow solid.

Step b:

Following the procedure described for step d in Example 2, phenol 11b (78.6 mg, 0.36 mmol) and alcohol 11c (80 mg, 0.25 mmol) gave compound 129 (39 mg, 30% yield) as a white solid.

TABLE 1

| Entry # | R$^1$ | R$^2$ | R$^3$ | R$^4$ | Q | MS ES$^+$ (MH) |
|---|---|---|---|---|---|---|
| 101 | H | H | Me | Et | 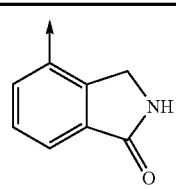 | 430 |

TABLE 1-continued
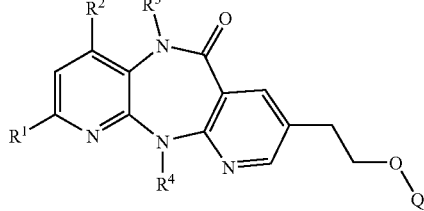
| Entry # | R¹ | R² | R³ | R⁴ | Q | MS ES⁺ (MH) |
|---|---|---|---|---|---|---|
| 102 | H | Me | H | Et | 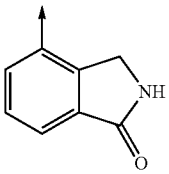 | 430 |
| 103 | H | H | Me | Et | 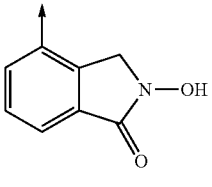 | 446 |
| 104 | H | H | Me | Et | 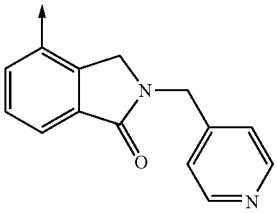 | 521 |
| 105 | H | H | Me | Et | 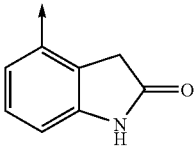 | 430 |
| 106 | H | H | Me | Et | 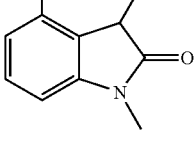 | 458 |
| 107 | H | H | Me | Et | 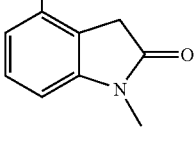 | 444 |
| 108 | H | H | Me | Et | 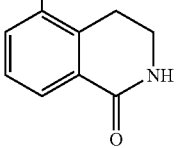 | 444 |

TABLE 1-continued
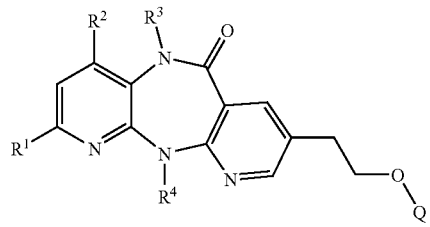
| Entry # | R¹ | R² | R³ | R⁴ | Q | MS ES⁺ (MH) |
|---|---|---|---|---|---|---|
| 109 | H | Me | H | Et | | 444 |
| 110 | H | H | Me | Et | | 445 |
| 111 | H | Me | H | Et | | 445 |
| 112 | H | H | Me | Et | | 473 |
| 113 | H | H | Me | Et | | 459 |
| 114 | H | Me | H | c-Pr | | 457 |
| 115 | H | Me | H | Et | | 473 |

TABLE 1-continued

| Entry # | R¹ | R² | R³ | R⁴ | Q | MS ES⁺ (MH) |
|---|---|---|---|---|---|---|
| 116 | H | Me | H | Et | 1-methyl-3,4-dihydroquinazolin-2(1H)-one (8-yl) | 459 |
| 117 | H | H | Et | Et | 3,4-dihydroquinazolin-2(1H)-one (8-yl) | 459 |
| 118 | H | H | Me | Et | 1-(carboxymethyl)-3,4-dihydroquinazolin-2(1H)-one (8-yl) | 503 |
| 119 | H | H | Me | Et | 1-methyl-3,4-dihydroquinazolin-2(1H)-one (6-yl) | 459 |
| 120 | H | H | Me | Et | 1,3-dimethyl-3,4-dihydroquinazolin-2(1H)-one (6-yl) | 473 |
| 121 | H | H | Me | Et | 3,4-dihydropyrido[2,3-d]pyrimidin-2(1H)-one | 445 |
| 122 | H | H | Me | Et | 1H-benzimidazol-2(3H)-one | 431 |
| 123 | H | H | Me | Et | 3,4-dihydroisoquinolin-1(2H)-one | 444 |

TABLE 1-continued

| Entry # | R¹ | R² | R³ | R⁴ | Q | MS ES⁺ (MH) |
|---|---|---|---|---|---|---|
| 124 | H | H | Me | Et | (3,4-dihydro-2H-benzo[e][1,3]oxazin-2-one, 5-yl) | 446 |
| 125 | H | H | Me | Et | (4,4-dimethyl-1H-benzo[d][1,3]oxazin-2(4H)-one, 5-yl) | 474 |
| 126 | H | H | Me | Et | (1H-benzo[d][1,3]oxazin-2(4H)-one, 5-yl) | 446 |
| 127 | H | Me | H | Et | (1H-benzo[d][1,3]oxazin-2(4H)-one, 5-yl) | 446 |
| 128 | H | H | Me | Et | (N-CH₂CO₂H substituted benzo[d][1,3]oxazin-2-one pyridyl) | 504 |
| 129 | F | Me | H | Et | (2-tert-butyl-benzo[d]isoxazol-3(2H)-one, 5-yl) | 506 |
| 130 | F | Me | H | Et | (2-methyl-benzo[d]isoxazol-3(2H)-one, 5-yl) | 464 |

TABLE 1-continued

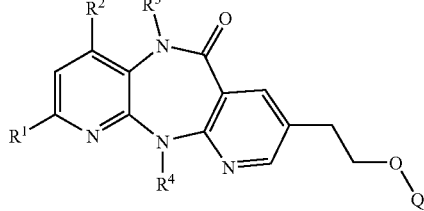

| Entry # | R¹ | R² | R³ | R⁴ | Q | MS ES⁺ (MH) |
|---|---|---|---|---|---|---|
| 131 | H | H | Me | Et | 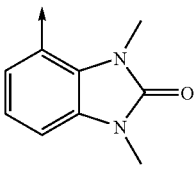 | 459 |
| 132 | H | H | Me | Et | 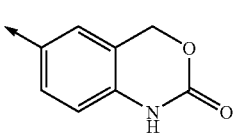 | 445 |
| 133 | H | H | Me | Et | 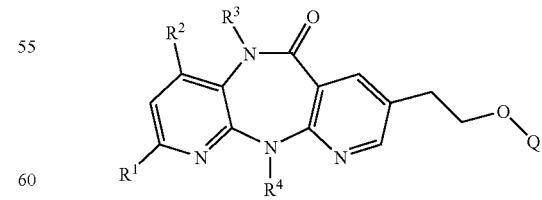 | 446 |

Reverse Transcriptase (RT) and Cell-Based Assays

The assays are as described in WO 01/96338A1, the contents of which are hereby incorporated herein.

The results are listed in Table 2 as $IC_{50}$(nM) and $EC_{50}$ (nM).

TABLE 2

| Entry # | $IC_{50}$ WT | $IC_{50}$ K103N/Y181C | $EC_{50}$ WT | $EC_{50}$ 103/181 |
|---|---|---|---|---|
| 101 | C | A | C | C |
| 102 | C | A | C | C |
| 103 | B | A | C | B |
| 104 | C | B | NT | NT |
| 105 | B | A | NT | NT |
| 106 | B | A | NT | NT |
| 107 | B | NT | NT | NT |
| 108 | C | B | NT | NT |
| 109 | C | A | NT | NT |
| 110 | C | A | C | C |
| 111 | C | A | C | B |
| 112 | C | A | C | B |
| 113 | C | C | C | C |
| 114 | C | A | NT | NT |
| 115 | C | A | NT | NT |
| 116 | C | A | NT | NT |
| 117 | C | A | NT | NT |
| 118 | C | A | A | A |
| 119 | C | A | NT | NT |
| 120 | C | A | NT | NT |
| 121 | B | A | NT | NT |
| 122 | B | A | NT | NT |
| 123 | C | C | NT | NT |
| 124 | C | C | NT | NT |
| 125 | B | A | NT | NT |
| 126 | C | A | NT | NT |
| 127 | C | A | NT | NT |
| 128 | B | A | NT | NT |
| 129 | B | A | NT | NT |
| 130 | C | A | NT | NT |
| 131 | B | A | NT | NT |
| 132 | B | A | NT | NT |
| 133 | C | A | NT | NT |

Table legend:
$IC_{50}$ (nM) A = >100 nM; B = 100–50 nM; C = <50 nM
$EC_{50}$ (nM) A > 50 nM; B = 10–50 nM; C < 10 nM; NT = not tested

The invention claimed is:

1. A compound represented by formula I:

(I)

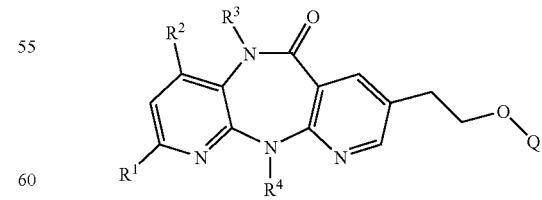

wherein
R¹ is selected from the group consisting of H, halogen, $(C_{1-4})$alkyl, $O(C_{1-6})$alkyl, and haloalkyl;
R₂ is H or $(C_{1-4})$alkyl;
R³ is H or $(C_{1-4})$alkyl;

$R^4$ is $(C_{1-4})$alkyl, $(C_{1-4})$alkyl$(C_{3-7})$cycloalkyl, or $(C_{3-7})$cycloalkyl; and Q is a fused phenyl-5 or 6-membered saturated heterocycle having one to two heteroatoms selected from O and N, said Q is selected from the group consisting of:

a)

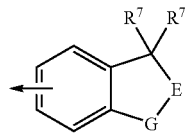

wherein one of E and G is C(O) and the other is $NR^5$ wherein $R^5$ is selected from the group consisting of H, hydroxy and $(C_{1-4})$alkyl unsubstituted or substituted with pyridinylmethyl, (pyridinyl-N-oxide)methyl or $C(O)OR^6$ wherein $R^6$ is H or $(C_{1-4})$alkyl; and each $R^7$ is independently H, Me or Et; or b)

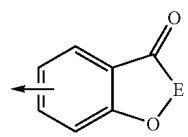

wherein E is $NR^8$ wherein $R^8$ is H, $(C_{1-4})$alkyl unsubstituted or substituted with $C(O)OR^9$ wherein $R^9$ is H or $(C_{1-4})$alkyl; or c)

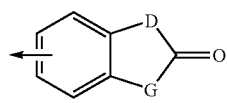

wherein D and G are $NR^{10}$ wherein each $R^{10}$ is independently H or $(C_{1-4})$alkyl unsubstituted or substituted with $C(O)OR^{11}$ wherein $R^{11}$ is H or $(C_{1-4})$alkyl; or d)

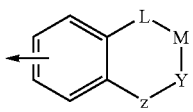

wherein one of L, M, Y and Z is $NR^{12}$ wherein $R^{12}$ is H, $(C_{1-4})$alkyl unsubstituted or substituted with $C(O)OR^{12x}$ wherein $R^{12x}$ is H or $(C_{1-4})$alkyl; one of the remaining positions of L, M, Y and Z adjoining the $NR^{12}$ is C(O); and the remaining two positions are each $CR^{13}R^{13}$ wherein each $R^{13}$ is independently H, Me or Et; or e)

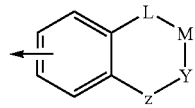

wherein three adjoining positions of L, M, Y and Z (namely L-M-Y or M-Y-Z) represent $NR^{14}$—C(O)—O— or —$NR^{15}$—C(O)—$NR^{16}$— wherein $R^{14}$, $R^{15}$ and $R^{16}$ each represents H or $(C_{1-4})$alkyl unsubstituted or substituted with $C(O)OR^{17}$ wherein $R^{17}$ is H or $(C_{1-4})$alkyl; and the remaining position of L, or Z is $CR^{18}R^{18}$ wherein each $R^{18}$ is H, Me or Et;

or a pharmaceutically acceptable salt, thereof.

2. The compound according to claim 1, wherein $R^1$ is selected from: H, Cl, F, $(C_{1-4})$alkyl and $CF_3$; $R^2$ and $R^3$ is each independently H or Me; $R^4$ is ethyl or cyclopropyl; and Q is selected from:

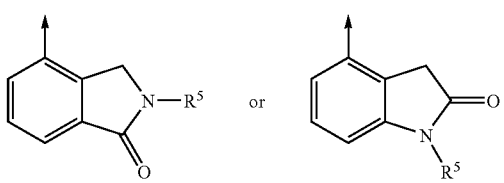

wherein $R^5$ is H, hydroxy, $CH_3$ or (4-pyridinyl)methyl;

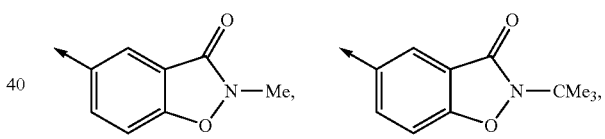

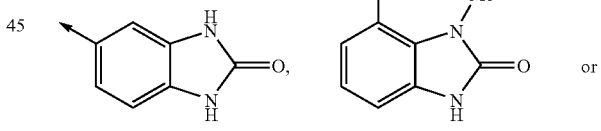

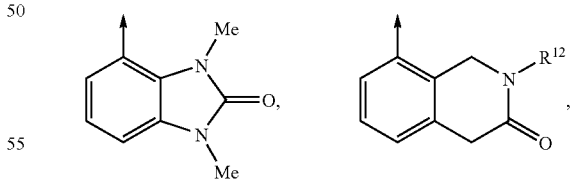

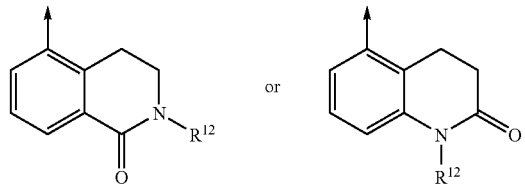

wherein $R^{12}$ is H, Me or $CH_2C(O)OH$, or Q is further selected from:

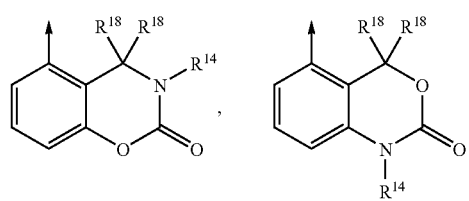

wherein $R^{14}$ is H, Me or $CH_2C(O)OH$ and each $R^{18}$ is independently H or Me;

or Q is further selected from:

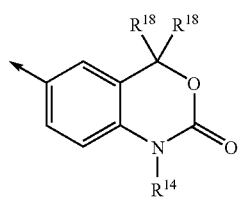

wherein $R^{15}$ is H, Me or $CH_2C(O)OH$ and $R^{16}$ is H, Me or $CH_2C(O)OH$.

3. The compound according to claim 2, wherein $R^1$ is H, Cl, F or Me; $R^2$ is H; $R^3$ is Me; $R^4$ is ethyl; and Q is selected from:

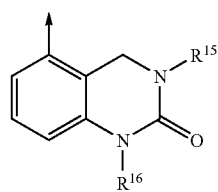

wherein $R^5$ is H, hydroxy or (4-pyridinyl)methyl;

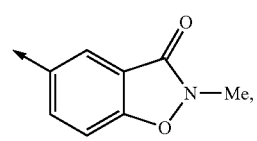 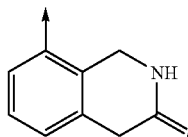

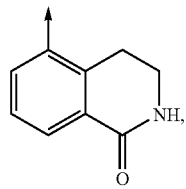 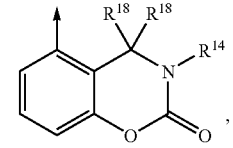

-continued

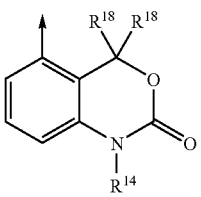 or 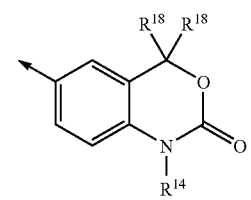

wherein $R^{14}$ is H or $CH_2C(O)OH$ and each $R^{18}$ is H, or

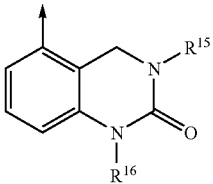 or 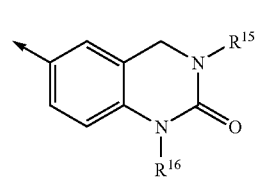

wherein $R^{15}$ is H or $CH_3$ and $R^{16}$ is H, $CH_3$ or $CH_2C(O)OH$.

4. The compound according to claim 3, wherein Q is selected from:

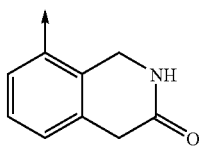 or 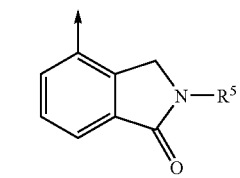

wherein $R^5$ is H or hydroxy,

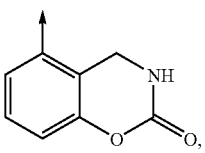 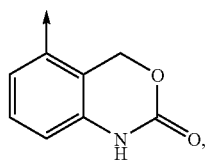

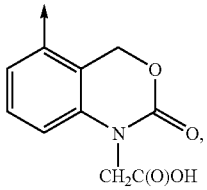 

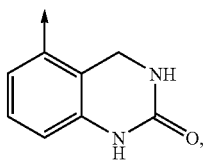 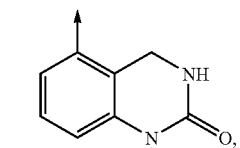

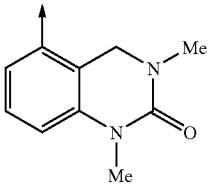 or 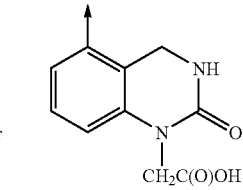

5. The compound according to claim 4, wherein $R^1$ is H, $R^2$ is H, $R^3$ is Me, $R^4$ is ethyl and Q is selected from:

6. A pharmaceutical composition for the treatment of HIV infection, comprising a compound of formula I according to claim 1, or a pharmaceutically acceptable salt thereof, and a pharmaceutically acceptable carrier.

7. A method for the treatment of HIV infection, comprising administering to a patient an HIV inhibiting amount of a compound of formula I according to claim 1, or a pharmaceutically acceptable salt thereof.

8. A method for the treatment of HIV infection, comprising administering to a patient an HIV inhibiting amount of a pharmaceutical composition, according to claim 6.

9. A method for preventing perinatal transmission of HIV-1 from mother to baby, comprising administering a compound of formula I according to claim 1, to the mother before giving birth.

10. A process for producing a compound of formula I according to claim 1, comprising steps of:

coupling a compound of formula 2:

wherein $R^1$, $R^2$, $R^3$ and $R^4$ are as defined in claim 1;
with a phenolic derivative selected from:

a)

wherein one of E and G is C(O) and the other is $NR^{5A}$ wherein $R^{5A}$ is a N-protecting group, hydroxy or $(C_{1-4})$ alkyl unsubstituted or substituted with pyridylmethyl, (pyridinyl-N-oxide) methyl or $C(O)OR^{6A}$ wherein $R^{6A}$ is a carboxy protecting group or $(C_{1-4})$alkyl; and each $R^7$ is independently H, Me or Et.

b)

wherein E is $NR^{8A}$ wherein $R^{8A}$ is a N-protecting group, $(C_{1-4})$alkyl unsubstituted or substituted with $C(O)OR^{9A}$ wherein $R^{9A}$ is a carboxy protecting group or $(C_{1-4})$alkyl; or c)

wherein D and G each independently is $NR^{10A}$ wherein $R^{10A}$ is a N-protecting group or $(C_{1-4})$alkyl unsubstituted or substituted with $C(O)OR^{11A}$ wherein $R^{11A}$ is a carboxy protecting group or $(C_{1-4})$alkyl;

d)

wherein one of L, M, Y and Z is $NR^{12A}$ wherein $NR^{12A}$ is a N-protecting group, $(C_{1-4})$alkyl unsubstituted or substituted with $C(O)OR^{12y}$ wherein $R^{12y}$ is a carboxy protecting group or $(C_{1-4})$alkyl; one of the remaining positions of L, M, Y and Z adjoining the $NR^{12A}$ is C(O); and the remaining two positions are each $CR^{13}R^{13}$ wherein each $R^{13}$ is independently H, Me or Et; or e)

wherein three adjoining positions of L, M, Y and Z (namely L-M-Y or M-Y-Z) represent —$NR^{14}$—C(O)—O— or —$NR^{15}$—C(O)—$NR^{16}$— wherein $R^{14}$, $R^{15}$ and $R^{16}$ are as defined in claim 1, and the remaining position of L or Z is $CR^{18}R^{18}$ wherein each $R^{18}$ is as defined in claim 1;

and, if required, removing any protective groups in a mixture of aqueous base or aqueous acid in a co-solvent, to obtain the corresponding compound of formula I.

* * * * *